(12) United States Patent
Schildroth et al.

(10) Patent No.: US 10,492,361 B2
(45) Date of Patent: Dec. 3, 2019

(54) APPARATUS, SYSTEM AND METHOD FOR GENERATING CROP NUTRIENT PRESCRIPTIONS

(71) Applicant: 360 Yield Center, LLC, Morton, IL (US)

(72) Inventors: Rhett Warren Schildroth, North Liberty, IA (US); Ron Lloyd, Girard, IL (US)

(73) Assignee: 360 Yield Center, LLC, Morton, IL (US)

( * ) Notice: Subject to any disclaimer, the term of this patent is extended or adjusted under 35 U.S.C. 154(b) by 437 days.

(21) Appl. No.: 15/168,502

(22) Filed: May 31, 2016

(65) Prior Publication Data
US 2016/0270289 A1    Sep. 22, 2016

Related U.S. Application Data

(63) Continuation-in-part of application No. 14/253,926, filed on Apr. 16, 2014.

(60) Provisional application No. 62/277,391, filed on Jan. 11, 2016, provisional application No. 62/168,649, filed on May 29, 2015, provisional application No. 61/827,620, filed on May 26, 2013.

(51) Int. Cl.
*A01C 21/00* (2006.01)
*G01N 33/00* (2006.01)
*G01N 33/24* (2006.01)
*G01S 19/13* (2010.01)

(52) U.S. Cl.
CPC ....... *A01C 21/007* (2013.01); *G01N 33/0098* (2013.01); *G01N 33/24* (2013.01); *G01S 19/13* (2013.01); *G01N 2033/243* (2013.01); *G01N 2033/245* (2013.01)

(58) Field of Classification Search
CPC ............. G01N 33/24; G01N 2033/245; G01N 2033/243; A01C 21/007
See application file for complete search history.

(56) References Cited

U.S. PATENT DOCUMENTS

| | | | |
|---|---|---|---|
| 5,038,040 A | 8/1991 | Funk et al. | |
| 6,044,324 A * | 3/2000 | Boerhave | E02D 1/00 702/5 |
| 6,356,830 B1 | 3/2002 | Adamchuck et al. | |

(Continued)

OTHER PUBLICATIONS

Adsett, J.F. et al., Development of an Automated On-the-Go Soil Nitrate Monitoring System, Article in Applied Engineering in Agriculture, 1999, pp. 351-356, vol. 15(4).

(Continued)

*Primary Examiner* — Paul M. West
(74) *Attorney, Agent, or Firm* — Thomas J. Oppold; Larkin Hoffman Daly & Lindgren, Ltd.

(57) ABSTRACT

An apparatus, system and method for generating crop nutrient prescriptions utilizing a portable soil testing apparatus. The portable soil testing apparatus includes at least one soil sensor for identifying soil properties of plurality of soil samples collected within a field zone associated with a GPS location. A computing device in signal communication with the at least one soil sensor generates the crop nutrient prescription for the field zone based on the identified soil properties of the collected soil samples and may further be based on input of various agronomic factors.

9 Claims, 30 Drawing Sheets

(56) References Cited

U.S. PATENT DOCUMENTS

| | | | |
|---|---|---|---|
| 6,937,939 B1* | 8/2005 | Shibusawa | G01N 21/314 250/255 |
| 7,216,555 B2 | 5/2007 | Drummond et al. | |
| 8,204,689 B2 | 6/2012 | Christy et al. | |
| 2003/0112152 A1 | 6/2003 | Pickett | |
| 2012/0103077 A1* | 5/2012 | Koshnick | G01N 33/24 73/64.56 |
| 2013/0258317 A1 | 10/2013 | Preiner et al. | |

OTHER PUBLICATIONS

Bender, Ross, Modem Corn Hybrids' Nutrient Uptake Patterns, Article in Better Crops, 2013, pp. 7-10, vol. 97(1).

* cited by examiner

FIG. 12

CALIBRATE

STEP 2 OF 3
Soak Sensor

1. Remove the storage bottle from the shelf (36) below the Sensor Station (30)

Fill the small Calibration and Overnight Bottle to the fill line with the nitrate standard solution.

Note: Use fresh nitrate standard solution each day you operate the machine. The nitrate standard solution can be reused for multiple analysis in a day if not contaminated by a wet or dirty sensor.

2. Immerse sensor in the nitrate standard solution by placing the Calibration and Overnight Bottle onto the shelf (36)

Soaking the sensor corrects sensor drift, ensuring repeatable and accurate results.

< Back    Next Step: Calibrate Sensor

| CALIBRATE | ANALYZE | ALL RESULTS | SETTINGS |

FIG. 13

ALL RESULTS

| Farmer | Farm | Field | Field Analysis | |
|---|---|---|---|---|
| > Smith | 1 | 1-1 | | Export |
| ∨ Smith | 2 | 2-1 | | Export |

001
5/26/15
Depth
Core Length: 6 in

1
5/21/15
Depth: 6 in
Core Length: 6 in

| | | | | |
|---|---|---|---|---|
| > Jones | Jones | SW Field | | Export |
| > Johnson | Johnson | Home | | Export |
| > Miller | Miller | West Field | | Export |

Export All Results    Export & Delete All Results

| CALIBRATE | ANALYZE | ALL RESULTS | SETTINGS |

Estimated Corn N-Need

1. Enter yield potential:　　　　　　　　　　Your soil analysis nitrogen results

| 70 | bu/acre

| 20 PPM | Core Length 12 in |

2. Select growth stage when the soil sample was taken

— Nitrogen use over time

Missing Core Length
   Please enter a core length in inches

[Cancel]　　[OK]

VE　V3　V6　V9　V12　V15　V18　R1　R6

| VE | Seeding has emerged
   At this stage, your crop has used 0% of its total Nitrogen need. |

How to determine Growth Stages >

3. Enter your soil's organic matter:

| 0.0 | % organic matter

FIG. 21

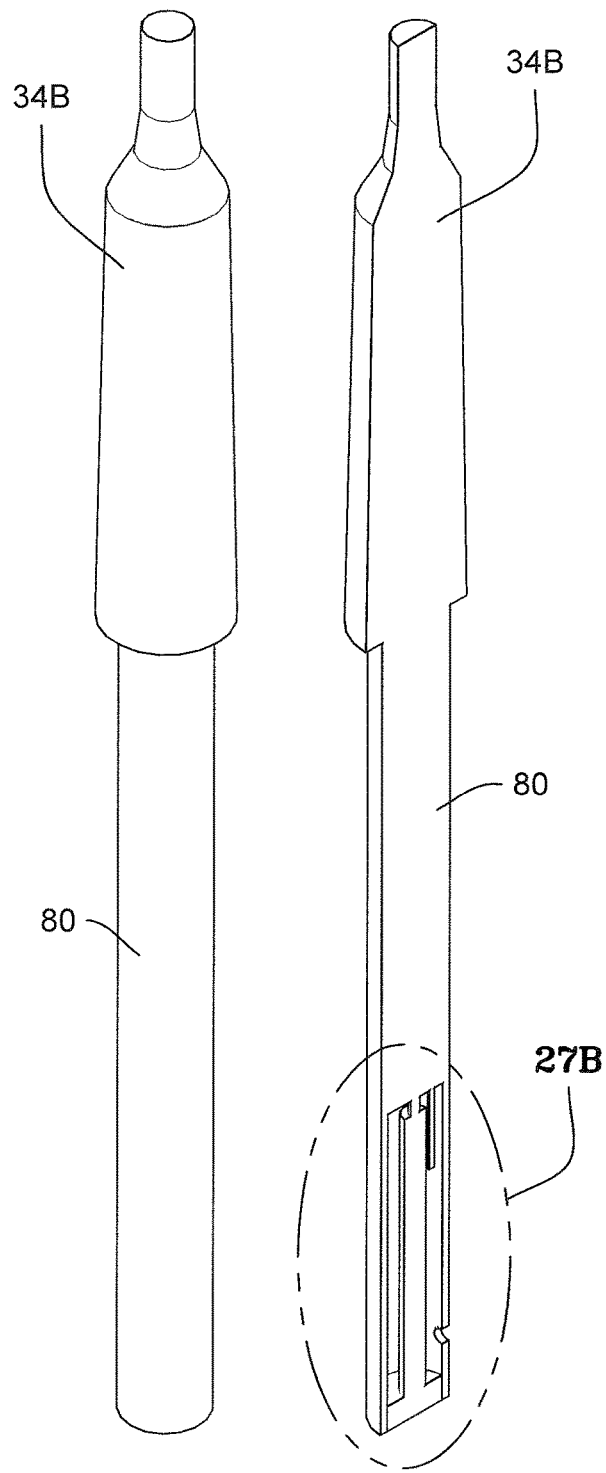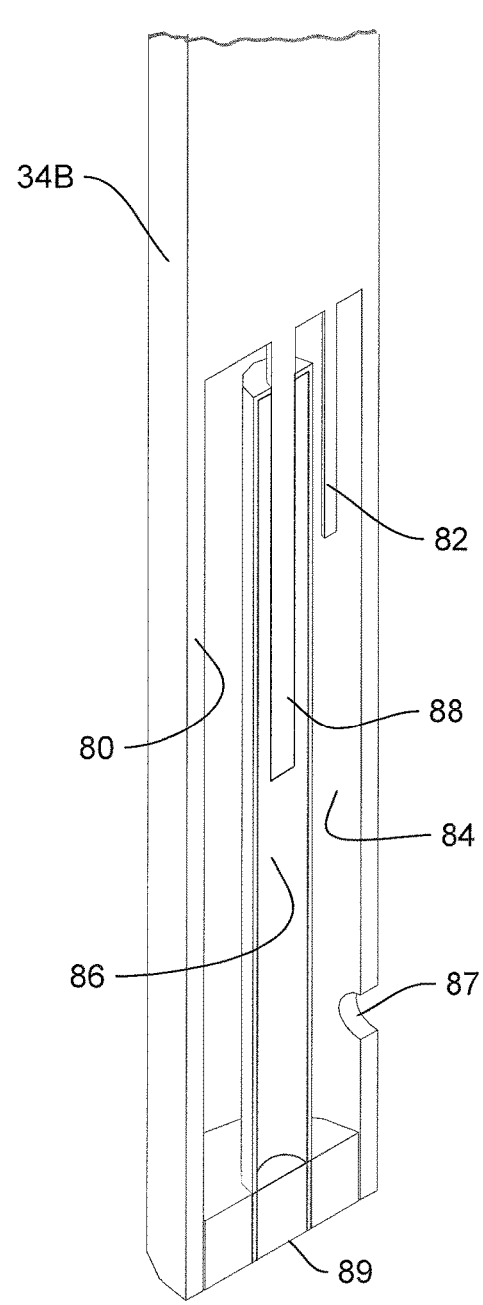
FIG. 27  FIG. 27A  FIG. 27B

Table 1

| K% Nitrogen Consumption by Corn Over Complete Growing Season |||||| 
|---|---|---|---|---|---|
| Growth Stage | % | Growth Stage | % | Growth Stage | % |
| V2 | 1 | V10 | 18 | V18 | 63 |
| V3 | 2 | V11 | 22 | VT/R1 | 76 |
| V4 | 4 | V12 | 26 | R2 | 78 |
| V5 | 6 | V13 | 30 | R3 | 80 |
| V6 | 8 | V14 | 35 | R4 | 82 |
| V7 | 10 | V15 | 42 | R5 | 85 |
| V8 | 12 | V16 | 49 | R6 | 100 |
| V9 | 14 | V17 | 56 | | |

FIG. 30

APPARATUS, SYSTEM AND METHOD FOR GENERATING CROP NUTRIENT PRESCRIPTIONS

BACKGROUND

Chemical treatments are commonly applied to soil to deliver nutrients required by crops for optimal growth and production. For example, nitrogen-containing fertilizers such as ammonia and urea are commonly used by farmers to enhance corn crop yields. Soil can be treated during the growing or non-growing season, with most fertilizers typically being applied early in the growing season based on the consistency and moisture content and to avoid damage to growing crop.

The efficacy of chemical treatments can depend upon a number of factors. Such factors include, among others, the species and variety of crop being grown, the growth stage of the crop, the composition, moisture content, and pH of the soil, the presence of organic matter within the soil, weather conditions, hours of daylight, the nature of past and future chemical treatments, and the form and quantity of anticipated current chemical treatment.

For example, it is known that corn takes up, in the grain and stover, about one pound of nitrogen per bushel of grain produced. Only a small amount of this nitrogen is needed during the seedling stage of corn, while subsequent growth stages, such as the V8 growth stage, require significant higher quantities of nitrogen. Beginning with the V8 growth stage and continuing over a period of 30 days if conditions are favorable, corn can advance from approximately knee-high to the tassel stage of development. During this stage, corn may require over half its total nitrogen supply. Nitrogen deficiency at any time during a corn plant's life will impair yield. If the deficiency occurs during a rapid vegetative growth phase, however (such as at the beginning of the V8 growth stage), yield losses may be severe. It is therefore important to precisely determine the timing and amount of nitrogen applications. Accordingly, there is a need for a system that prescribes nitrogen or other nutrient and chemical applications based on the growth stage of a particular crop.

As another example, weather has a significant impact on the uptake of nutrients such as nitrogen by crops. In particular, temperature and moisture can impact the amount of nitrogen mineralized from the organic matter fraction of the soil. Excessive rainfall may cause nitrogen loss through leaching and saturation of the soil, causing the plant to run out of nitrogen prior to reaching rapid vegetative growth stages such as the V8 stage. Colder temperatures, such as those below 50 degrees Fahrenheit, generally cause soil microbial activity to be significantly slowed or stopped altogether. Excessively dry conditions may prevent nitrogen from moving from the point of application to the root zone of the plants.

Yet another important factor in the uptake of soil nutrients such as nitrogen is soil type. In particular, soil type plays an important role in determining soil moisture, including the water available to a plant. Differences in soil type can have a dramatic impact on the growth of a plant as well as its ability to recover from heat and moisture stress during different growth stages of its life cycle. Generally, sandy soils hold less water per foot of soil, subjecting plants to stress during dry periods. Clay soils hold more water than other soil textures, but plant roots are not able to extract the moisture needed from high-clay (small particle size) soils. Loamy soils provide the most usable amount of plant-available water per foot of soil. Soil type can therefore have a dramatic effect on the amount of residual nutrients remaining due to previous applications.

Additionally, the topography or terrain or slope (i.e., elevation change) across a field or within a zone or zones of a field can effect soil nutrient applications and so need to be considered along with previous and planned nitrogen applications.

The nature of past and future chemical treatments can also significantly affect the short-term and long-term projections for the nitrogen content soil. Common nitrogen fertilizers include anhydrous ammonia, urea-ammonium nitrate solutions, granular urea, ammonium nitrate and ammonium sulfate. Ammonium ($NH_{4+}$) forms of nitrogen bind to negatively charged soil particles and are not subject to leaching or dentrification losses. This means that applying nitrogen fertilizers that include more ammonium and less nitrate forms of nitrogen reduces the potential for loss in the short term. However, over time, soil microbes convert the ammonium to nitrate ($NO_{3-}$), which can be lost due to leaching or saturation during heavy or excessive rainfall. Urea-based fertilizers are also subject to loss through volatilization when surface applied. Volatilization potential is reduced when the urea is taken into the soil through rainfall, irrigation or tillage.

Accordingly, there is a need to model chemical application of crop nutrients based on current conditions and soil attributes that will allow farmers to reach desirable crop yield targets. There is a further need to develop prescriptions for such chemical applications in real time in conjunction with location-based soil sampling and analysis.

While location-based soil testing and analysis allows agricultural growers and providers to tailor seed variety and chemical applications to actual growing conditions, it has been difficult to obtain soil properties without the use of either large soil-collection machines or external laboratories. The use of external laboratories for soil testing is particularly problematic because soil samples must be sufficiently large to enable proper testing, must be removed and shipped from the site (thereby requiring appropriate labeling and tracking so that test results are accurately to the location of the sampling site). Additionally, soil testing at external laboratoriess is typically performed by drying out the soil sample, a process that can skew results.

An additional drawback to the use of external laboratories is the amount of time required to package, ship, and analyze a sample and report the corresponding results. Depending upon factors such as the locations of the sampling site and the laboratory, the day of the week on which shipment is made, and other externalities, such timeframes can range from several days to several weeks. During this time, changes may also occur to the soil sample and crops may be exposed to non-optimal soil conditions that can adversely affect desired crop yields. The detrimental effects of improper or unbalanced soil conditions can be particularly magnified during certain accelerated growth stages, such as the V8 stage for corn.

Automated soil collection devices have been developed that analyze soil on-location. Such automated soil analyzing machines are typically large attachments that must be pulled by the grower through the field of interest. Not only are such machines extremely expensive, but significant time is required to set up and attach the device to a tractor or other vehicle. Moreover, such devices generally cannot be used when crops are present due to the ensuing damage to the crops that would result during use. This restricts their operational usefulness to pre-planting or post-planting timeframes, effectively eliminating a farmer's ability to measure growing conditions during a plant's life cycle.

Furthermore, previous attempts to provide location-based soil analysis and sampling typically test the soil in a solid state. This may lead to potential damage to the analyzing sensors from rocks and other field debris. Others have attempted to address this issue. For example, U.S. Pat. No. 7,216,555 ("the '555 Patent") attempts to address the potential for abrasion and damage to the sensors by providing pressure sensitive measurements—essentially allowing the sensors to move in response to rocks and other field debris. While this may help to minimize potential damage to the sensors, the additional shock absorbing sensor mounts add expense, weight and complexity to the device. Moreover, because the device measures the soil in solid form and because rocks and field debris can vary the position of the sensors, the test results may not accurately reflect the true composition of the soil that is sampled. Therefore, there is a need for a soil-testing apparatus and method which avoids the expense, complexity, and potential inaccuracies that may occur with the apparatus disclosed in the '555 Patent.

Others have attempted to provide robotic vehicles with built-in soil-testing laboratories. For example, U.S. Publication Number 2003/0112152 ("the '152 Publication") discloses a robotic vehicle and method for soil testing. This system is a dedicated autonomous system. While such systems can determine soil properties by location autonomously, they are not easily transportable and they are expensive. Moreover, a user of such systems cannot easily perform random tests of soil properties or replicate identical tests upon the occurrence of unexpected results. Additionally, farmers may want to ascertain the soil condition of a particular area of interest while they are physically present in the field. If the farmer were using the autonomous system of the '152 Publication, for example, the farmer would have to call out the robot, direct it to the specific location, wait for the robot to arrive, perform testing and upload results so that the farmer could understand the soil conditions at the farmer's present location. Therefore, it would be desirable to provide farmers with the ability to test soil conditions while in the field without the need to call up a dedicated soil testing autonomous system.

It would also desirable to have a soil testing apparatus that is compact enough for easy transport to and within a field, one that tolerates dust and temperature fluctuations, one that can absorb shock loads and vibrations and one that allows for the sensor to be operated in the field at any time.

A further drawback of soil-analyzing systems is that they fail to provide actionable information and instead only provide a farmer with information concerning the current properties of a soil sample. Requiring the farmer or an agronomist to correlate the soil properties from the soil analysis using various charts or algorithms to produce usable output from which a crop nutrient prescription can be derived—such as a recommended nitrogen application—which a farmer can then apply. This can result in additional delays, added complexity, increased cost and greater risk of error.

Thus, there is a need in the art for an apparatus, system and method for soil testing that is portable, easy to use, prevents damage to sensors and allows for on-site or location-based testing. There is a further need in the art for a soil testing method and apparatus that can prescribe an optimal chemical application (such as anhydrous or urea ammonium nitrate (UAN)) based on certain measured parameters (such as a nitrate reading in pounds per square inch), user input of various agronomic factors (such as yield target, crop growth rate at the time of sampling, and sample depth) and constants and conversion factors via a user interface integrated or connectable to a soil testing device.

In particular, there is a need in the industry to enable farmers to generate nitrogen balance and nitrogen needs-prediction for an area of interest beginning at the time of sampling and continuing for the remainder of a growing season to allow a farmer to take appropriate action to address soil condition in near real time during the growing season. There is a further need for a soil-testing apparatus and method which can generate soil-sampling prescriptions for a field or an area of interest within the field. There is also a need for a soil-testing apparatus and method for receiving and displaying a soil-sampling prescription, including pathing to soil sampling locations within the soil sample-prescription for a field or an area of interest within the field.

DESCRIPTION OF THE DRAWINGS

FIGS. 12-23 are examples of various user interface screens.

FIG. 27 is a perspective view of a second sensor of the multiple sensor array of FIG. 25.

FIG. 27A is a cross-sectional view of the second sensor of FIG. 27.

FIG. 27B is an enlarged view of the circled portion of the second sensor of FIG. 27A.

FIG. 30 is a table showing $K_{\%}$ nitrogen consumption by corn over a complete growing season.

DESCRIPTION

Figure 1:
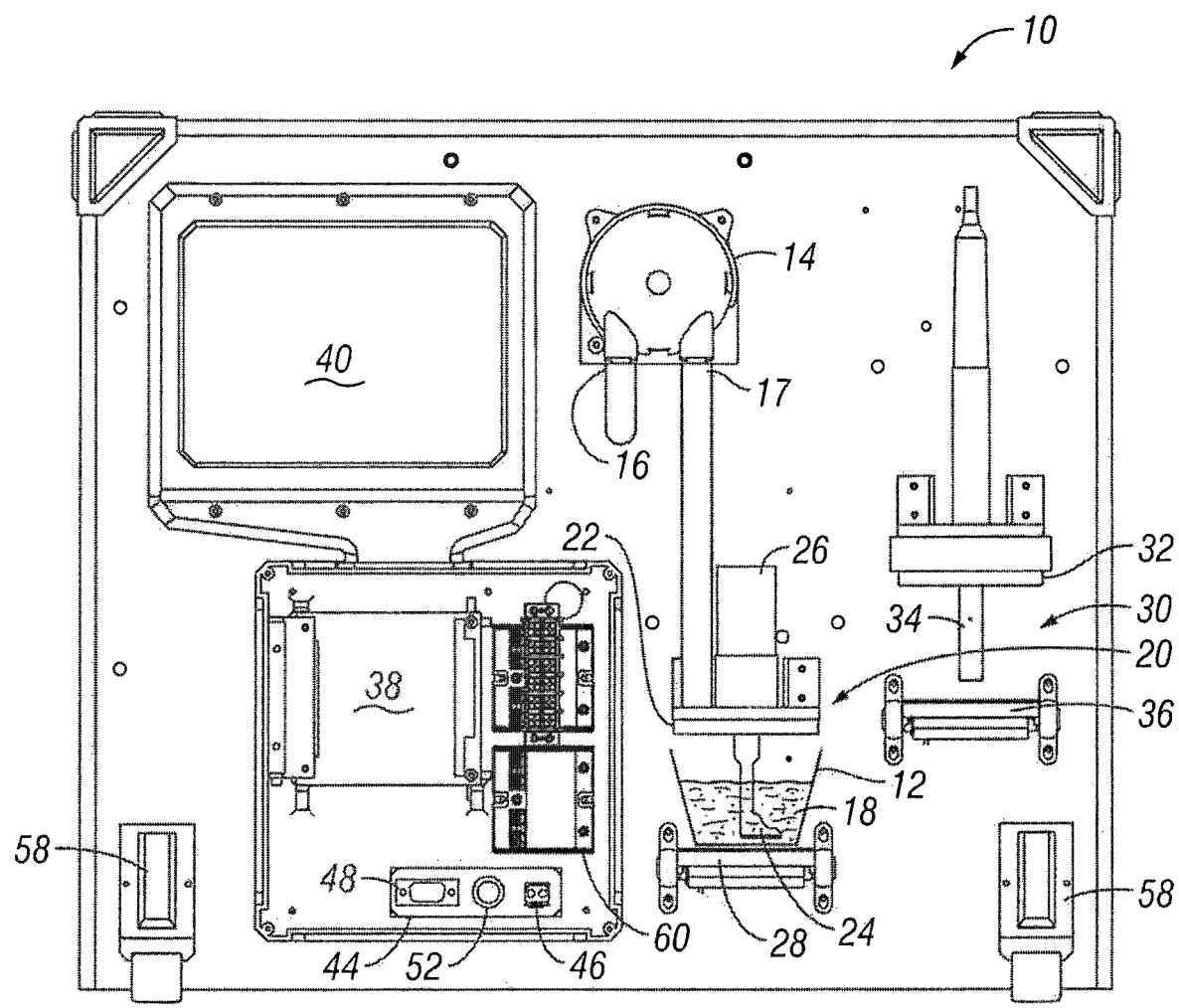
FIG. 1 is a front elevation view of one embodiment of a soil-testing apparatus.
Figure 2:
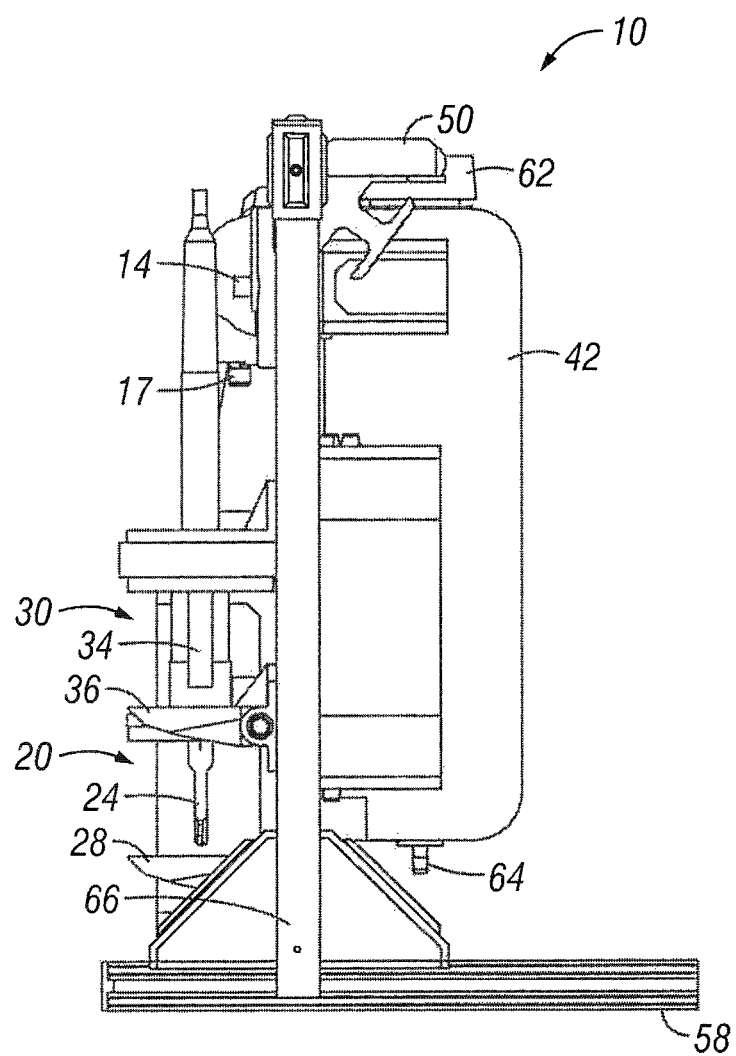
FIG. 2 is a side elevation view of the soil-testing apparatus of FIG. 1, secured to a portable base.
Figure 3:
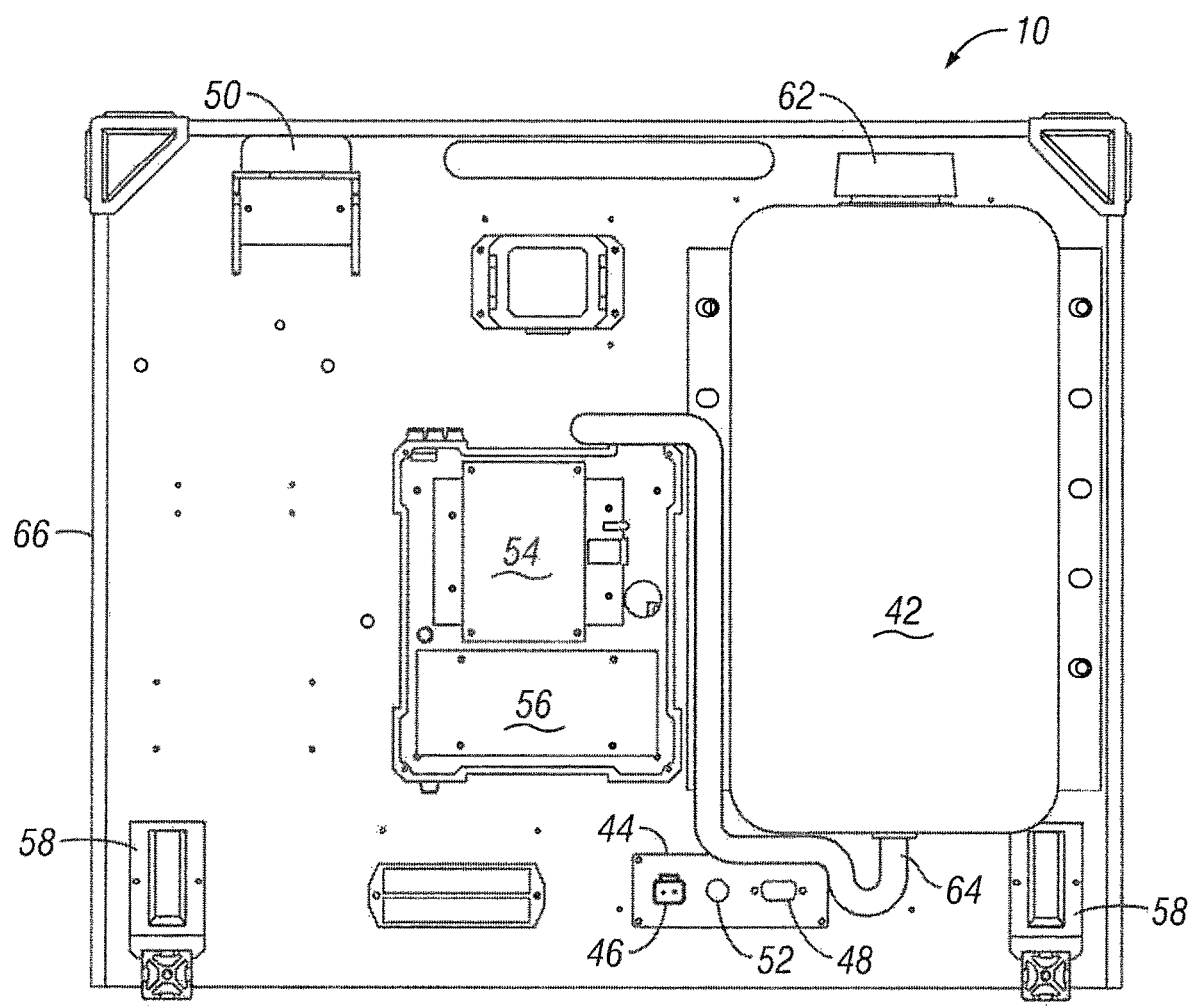
FIG. 3 is a rear elevation view of the soil testing apparatus of FIG. 1.

Referring to the drawings wherein like reference numerals designate the same or corresponding parts throughout the several views, FIGS. 1-3 illustrate an embodiment of a soil testing apparatus 10. FIGS. 4-10 and 24 illustrate alternative embodiments of the soil testing apparatus 10. The soil testing apparatus 10 is employed to analyze soil samples of a field or zone to determine soil properties, such as mineral or nutrient content, pH level, moisture content, salinity, pH level, humus (organic matter) content, etc., which are then utilized by the system 100 to generate a crop nutrient prescriptions taking into account different variables.

Soil-Testing Apparatus and Method

In use, referring to the various embodiments of the soil testing apparatus 10 as illustrated in FIGS. 1-3, 4-11 and 24, a soil sample is gathered and placed into a cup 12. The use of a standardized disposable cup (such as the well-known 5 oz. Dixie brand cups) keeps the sample size to a minimum while also keeping the soil sample container at a low cost. The apparatus 10 may include a pump 14, such as a peristaltic pump with an input 16 connected to the tank 42 by a hose and an outlet 17 that may add deionized water into the cup 12 at the stirring station 20. A calibrated amount of water (such as 2 oz.) can be added to ensure a general consistency of the soil sample slurry 18. The calibration can be adjusted by controlling the duration that the pump 14 operates or the amount of water added to the cup 12 may be determined based on volume or level indicators marked on the cup 12. The calibrated amount of water to be added to the cup 12 can also be determined based on weight utilizing a separate scale or by utilizing a load cell associated with the cup support platform 33 (identified below) to weigh the amount of added water added to the cup placed on the cup support platform, either prior to the soil sample being added or after the soil sample is added to the cup. In this latter example, the calibrated amount of water added would not be based on volume, rather it would be based on weight of the water as a function of the soil sample weight.

The cup 12 with the soil and water in it, is placed into the soil stirring station 20. The soil stirring station 20 generally includes a cup support platform 28, a stirring rod 24, and may include a reversible motor 26 operatively connected to turn the stirring rod 24. The cup support platform 28 may be mounted on a spring loaded or biased hinge to allow the user to press the cup support platform 28 down to insert the cup 12. The spring loaded hinge raises or biases the cup support platform 28 upwardly to support the cup 12 in relation to the stirring rod 24. Alternatively, the cup support platform 28 may slide up and down, either manually or operationally, using a slide track and motor (not shown). A cup holding ring 22 may be provided to restrain the cup to prevent it from moving during the stirring operation. Once the water has been added by the pump 14 at the soil stirring station 20, the motor 26 turns the stirring rod 24 to mix the soil and water to create the soil sample slurry 18. The stirring rod 24 may be made from a resilient plastic or metal and may be replaceable.

By having the stirring rod 24 mix the soil and water, rocks and field debris can settle out of the slurry, thus minimizing the potential damage to more sensitive components, such as the sensor 34. The soil stirring station 20 may be separate and apart from the soil sensor station 30. Alternatively, if a more compact design is desirable, the soil stirring station 20 and soil sensor station 30 may be combined where both the stirring rod 24 and the sensors of the sensor unit 34 will fit into the cup 12 at a single location. However, this may increases the chance of damaging the sensors with rocks or field debris commonly found in soil. To avoid such damage, the sensors of the sensor unit 34 may be removeably inserted into the cup 12 when testing is desired and removed from the cup 12 when not in use, such as during the stirring operation.

Alternatively still, multiple sensors can be used with one sample. Either multiple sensors can be immersed in the slurry at the same time or individual sensors may be inserted and removed automatically by a motor and track assembly (not shown) controlled by the computing device 38 to position and operate the appropriate sensor at the appropriate time.

At the soil sensor station 30, the cup 12 is placed onto the cup support platform 36 and the sensor(s) of the sensor unit 34 is/are sufficiently immersed into the soil sample slurry 18 for the sensors to operate effectively. The cup support platform 36 may be mounted on a spring loaded or biased hinge to allow the user to press the cup support platform 36 down to insert the cup 12. The spring loaded hinge raises or biases the cup support platform 36 upwardly to support the cup 12 in relation to the sensor unit 34. Alternatively, the soil sensor station 30 may include a cup support platform 36, which may slide up and down, either manually or operationally using a slide track and motor (not shown). A cup holding ring 32 may be provided to restrain the cup to prevent it from moving during the sensing operation.

The sensor unit 34 may comprise any known sensor(s) capable of reading or measuring a desired soil property. For example, the sensors of the sensor unit 34 may include an ion selective electrode, a near-infrared sensor to measure transmission or reflection of light in the near-infrared band, laser-induced-breakdown spectroscopy, or other light-based spectroscopy, as disclosed in U.S. Publication No. 2013/0258317, which is incorporated herein by reference in its entirety. The sensor unit 34 may provide an array of sensors with a common connector for ease of interchangability, such that the user can easily switch among the sensors to measure the property of interest (i.e., mineral or nutrient content, pH level, moisture content, salinity, humus content, etc.) in the soil slurry sample 18.

The sensor 34 is operatively connected to a computing device 38 with an integrated user interface, such as touch screen display 40 or a separate display screen with a keyboard or other user interface to which it is operatively connected. The computing device 38, display 40 and user interface may be an on-board system integrated into the apparatus 10 such as illustrated in FIGS. 1-3 or the computing device 38, display 40 and user interface may be a separate portable computing device 38 with a display 40 and user interface, such as a laptop, tablet, iPad, smartphone or other smart device that may connect or interface with the apparatus 10, such as shown in FIGS. 4-11 and 24. The computing device 38 is adapted or configured to accept inputs from any of the sensors of the sensor unit 34, and to perform necessary calculations based on the detections made by the sensors of the sensor unit 34 and/or data input by the user. It should be appreciated that a sensor unit 34 with a single sensor capable of measuring multiple soil properties may be used, and the computing device 38 may be configured or adapted to adjust the calculations as needed to measure the property of interest. In this manner the soil sensor station 30 is capable of measuring a variety of soil properties, such as analyzing the soil for different minerals or nutrients, including, but not limited to, potassium, phosphorus, nitrate nitrogen, ammonium nitrogen, manganese, bromide, Fluoride, Zinc, boron, molybdenum, calcium, magnesium, ammonia nitrogen, manganese, aluminum, nitrite nitrogen, sulfur, chloride, ferric iron, and copper as well as other soil properties, such as salinity, pH levels, humus content, etc.

Via the display screen 40, instructions can be displayed to walk the user through each step and track the user's progress. For example, when the user has a sample ready for the addition of water, the user can select the "add water" button. When the user then places the cup 12 in the stirring station 20, the user can select the "mix" button. After mixing, the user can transfer the cup 12 to the soil sensor station 30 for analysis and hit the "analyze" button.

If desired, the user can input the type of sensor 34 being used or simply request the measurement to be taken. For example, if the user asks for the nitrogen content of the sample 18, the computing device 38 is programmed to know the sensor 34 being used will detect the amount of nitrogen in the sample 18. The computing device 38 controls the system 100, responds to the user's inputs, displays the data, and saves the data preferably on a solid state data storage medium. Other types of data storage media may be used including standard hard drives and removable storage media, such as flash or USB drives. The computing device 38 may be connected to an on-board connector panel 44 that provides a power input 46, and may include an onboard GPS antenna, a GPS display input 48 and an onboard GPS signal input 52, if desired. Alternatively, instead of the GPS antenna being on-board the apparatus 10, the GPS could be provided by the portable computing device 38 (i.e., the laptop, iPad, tablet, smartphone, etc.) that the user connects to the apparatus 10. Thus, it should be appreciated, the compactness and portability of the soil testing apparatus 10 enables it to be positioned in close proximity of the soil sampling location to provide the user with the data for the soil conditions at that location. Alternatively, the farmer could carry a portable smart device (iPad, tablet, smartphone) having GPS capabilities and utilize a soil sample bag or container having a unique bar code that can be scanned by the smart device and associated with the GPS coordinates of each soil sample location. This would allow the farmer to walk the field or field zone and collecting the soil samples along the way by recording the GPS coordinates for each soil sample location using the smart device. Each collected soil sample would be placed in a separate bar coded bag or container that the farmer scans using the smart device which is programmed to associate the scanned bar code with the GPS coordinates. When the farmer returns to the soil testing apparatus 10 with the bar coded containers, the farmer can transmit/upload the GPS coordinates of the various soil samples from each barcoded bag or container to the computing device 38 (if a separate computing device is being used rather than the smart device being the computing device 38) such that the soil properties of each analyzed sample from the respective bar coded bags can be associated with the GPS coordinates.

Power may be provided to the power input 46 by a user's vehicle such as through a 110 volt connection. Alternatively, an on-board battery, such as a 12-volt battery, can be provided and integrated with the apparatus 10. If an on-board rechargeable battery is provided, the power input 46 can also recharge the battery as desired. The computing device 38 may have a wireless transceiver operatively connected to or integrated therewith it to enable communication over a cellular network, a wireless internet, a Bluetooth connection, or another type of wireless communication system. Referring to FIG. 3, an onboard circuit board 54 may convert analog sensor information to a digital format and provides signal outputs to the motor controller board 56. The motor controller board 56 controls the voltage outputs to operate the pump 14, mixing motor 26 and any slide motors that may be present.

The water tank 42 is also shown in FIG. 3. The water tank 42 is designed to hold a sufficient supply of water for the amount of intended testing and is refillable, preferably by the user. A cap 62 is provided to allow the water tank 42 to be refilled as necessary. Alternatively, the water tank 42 may be connected to a water source to ensure a constant supply of water, such as if, for example, the apparatus 10 is mounted onto a user's vehicle. A hose connection 64 is also preferably provided to connect the tank 42 to the pump 14. When no longer needed, the user can simply unhook the hose and allow the tank 42 to drain. This helps to reduce the weight of the apparatus 10, thereby making it easier to transport.

The apparatus 10 may be secured within a frame 66 that is made from a rigid metal or plastic. The various components of the apparatus 10, such as the computing device 38, the soil stirring station 20, the soil sensor station 30 and the water tank 42 may be secured within the frame 66 to a common support structure, such as a plastic board. The frame 66 provides protection and may include rubber or soft plastic edges or corners to minimize impact shock to the apparatus 10. One or more legs 58 may also be included to allow to provide additional stability when a user places the apparatus 10 on a surface. Alternatively, a case may be included that surrounds the components of the apparatus 10 and provides protection from adverse weather, dust, and travel conditions.

Figure 4:
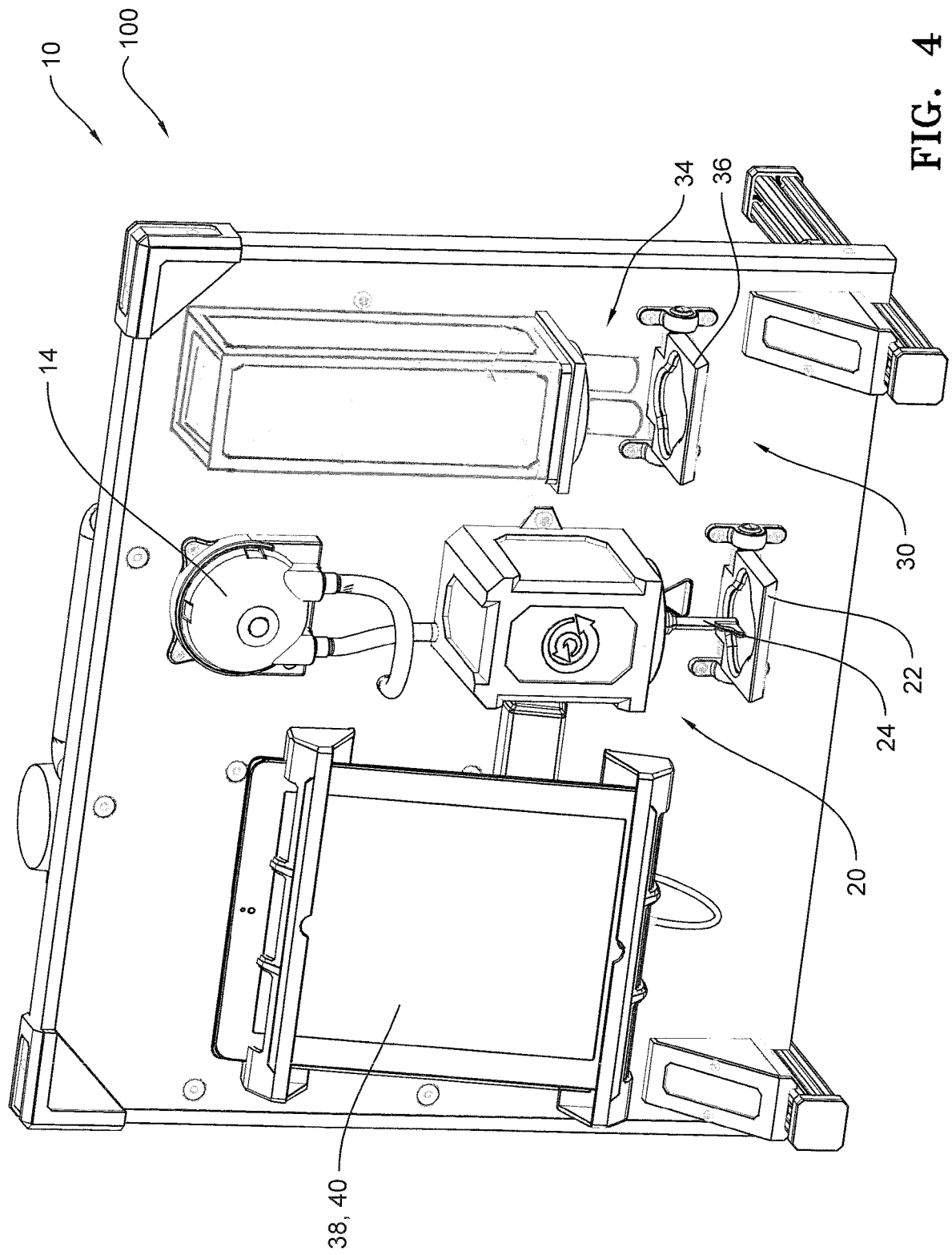
FIG. 4 is a front perspective view of another embodiment of a soil-testing apparatus.
Figure 5:
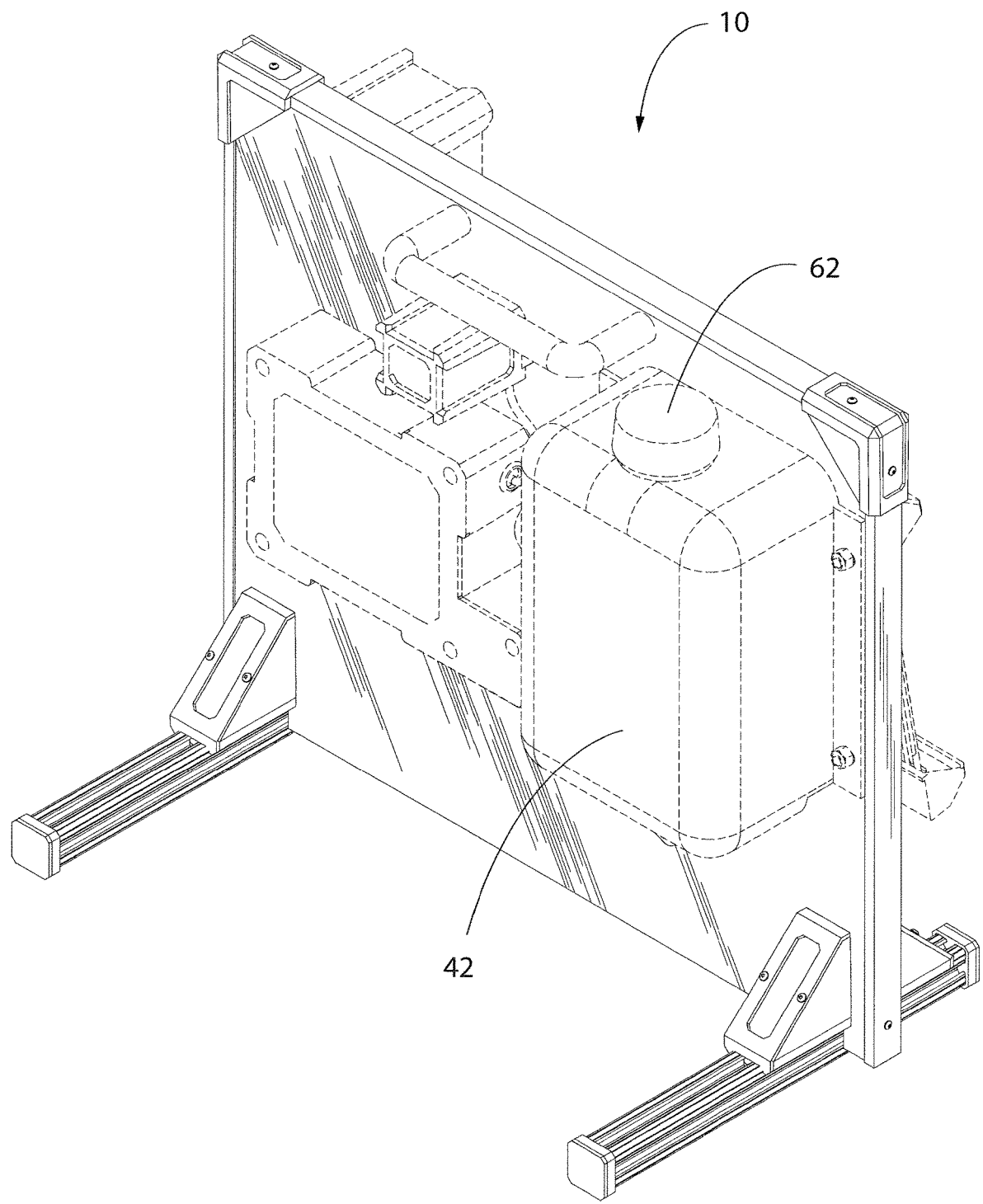
FIG. 5 is a rear perspective view of the soil-testing apparatus of FIG. 4.
Figure 6:
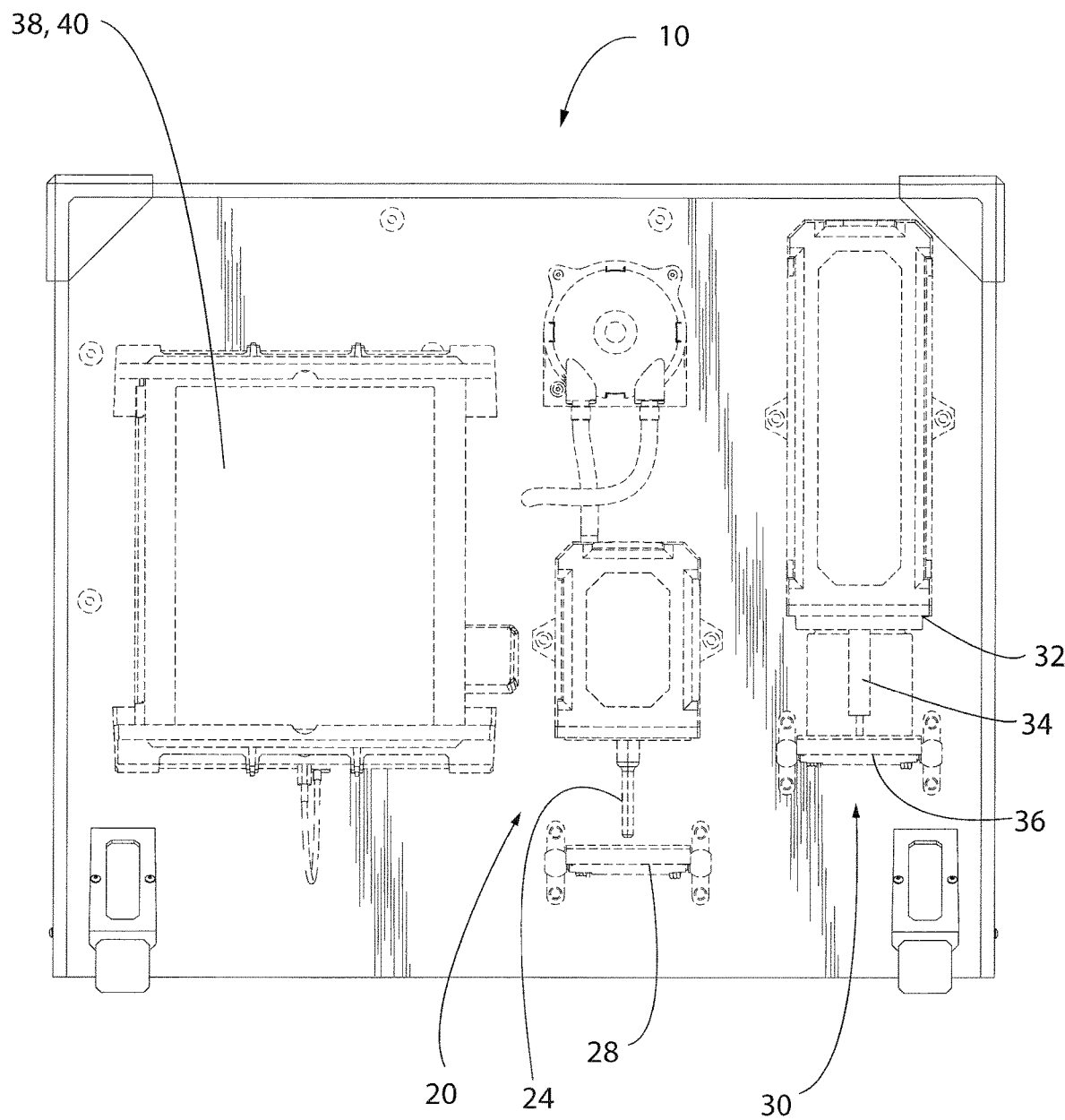
FIG. 6 is a front elevation view of the soil-testing apparatus of FIG. 4.
Figure 7:
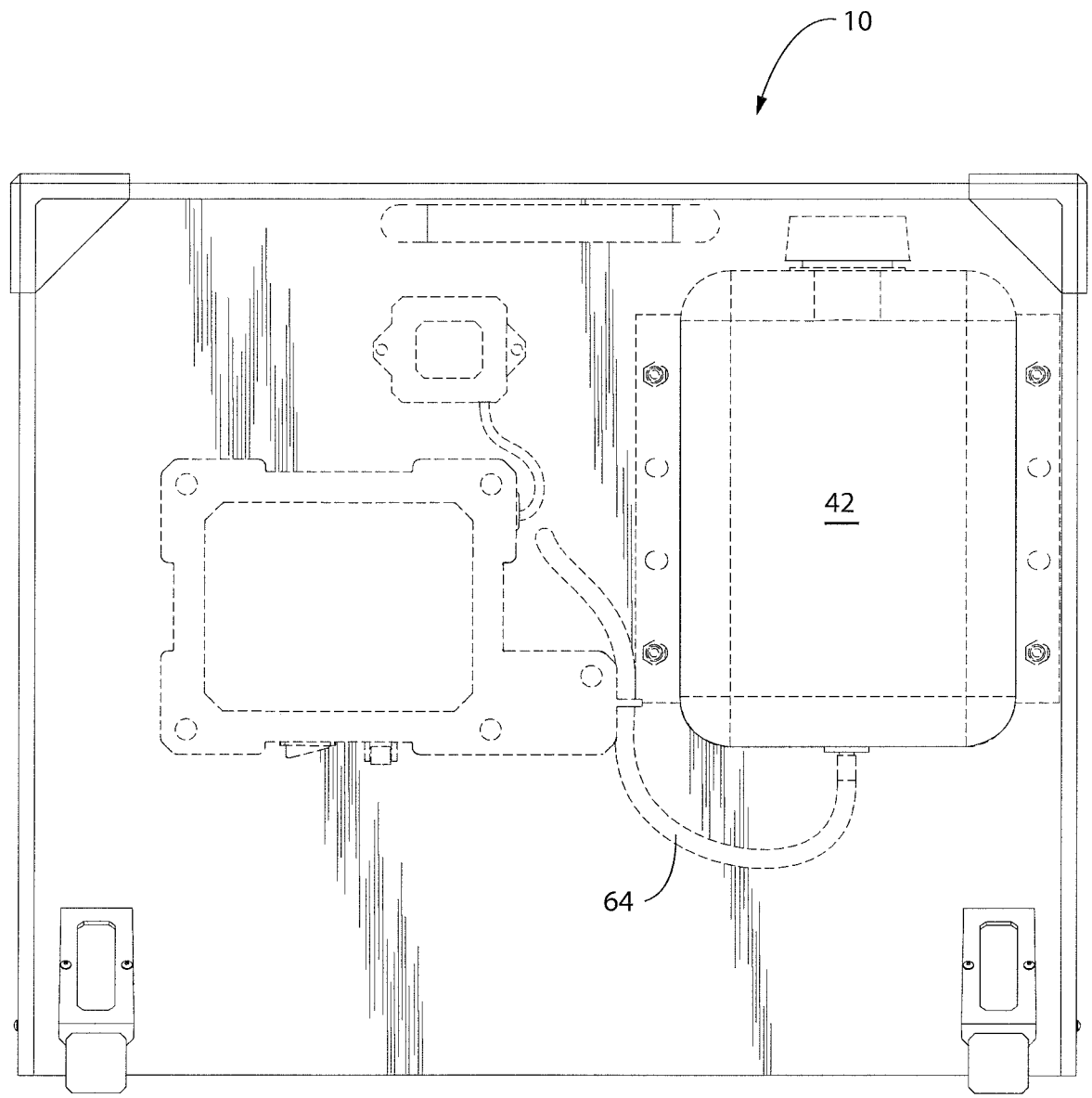
FIG. 7 is a rear elevation view of the soil-testing apparatus of FIG. 4.
Figure 8:
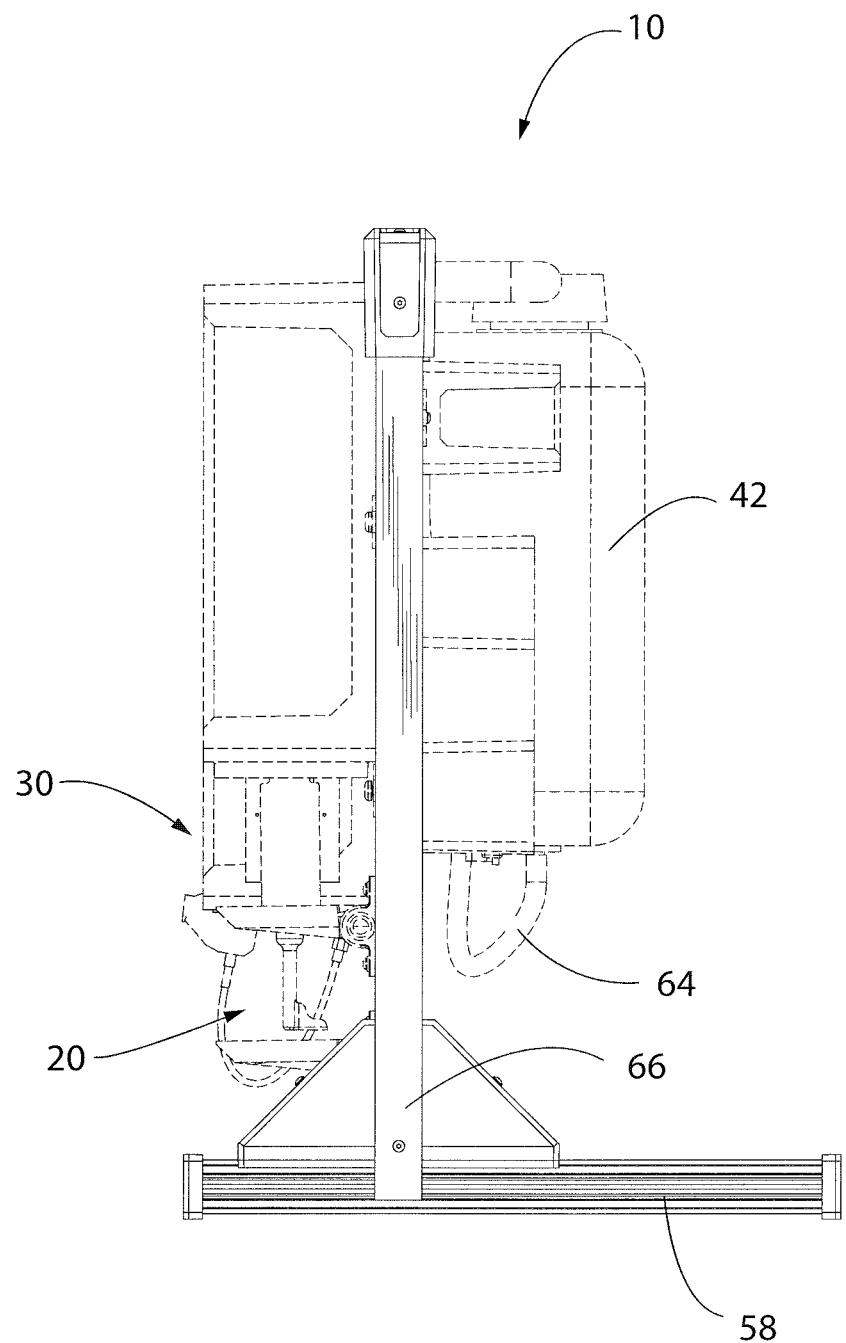
FIG. 8 is right side elevation view of the soil-testing apparatus of FIG. 4.
Figure 9:
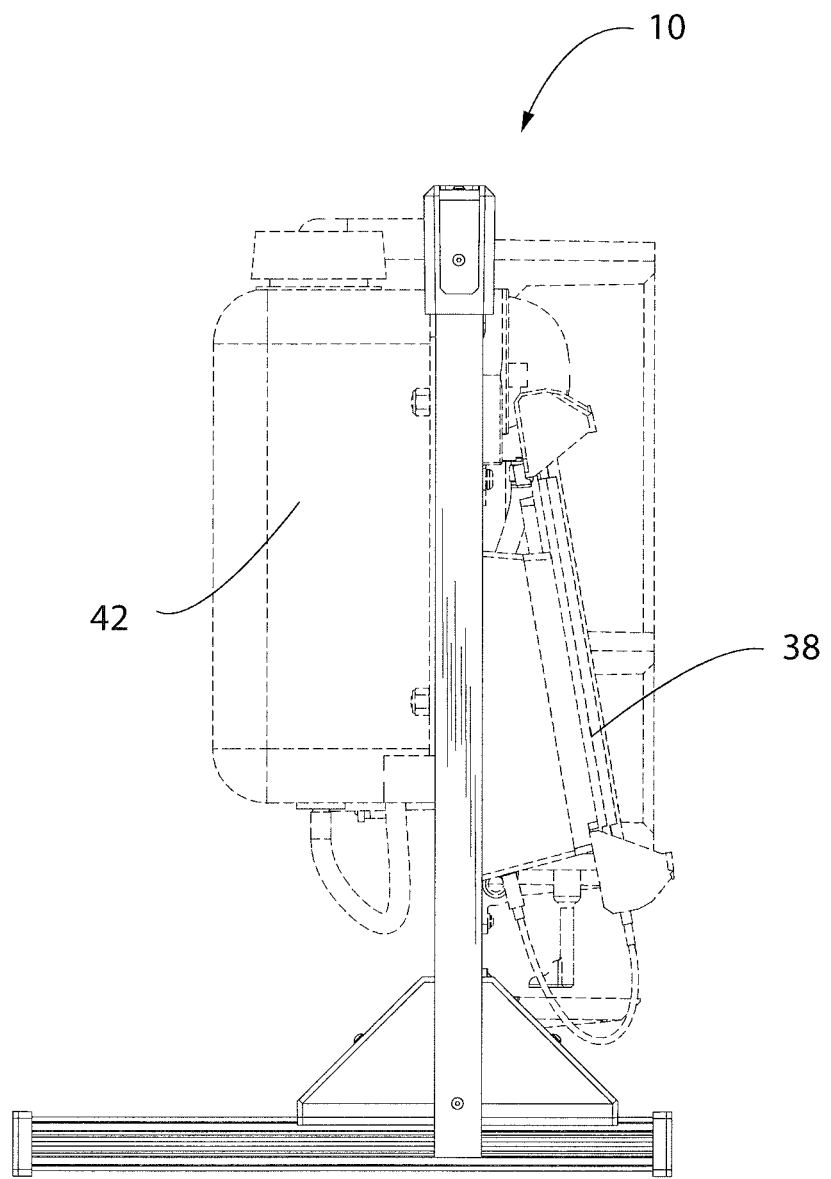
FIG. 9 is left side elevation view of the soil-testing apparatus of FIG. 4.
Figure 10:
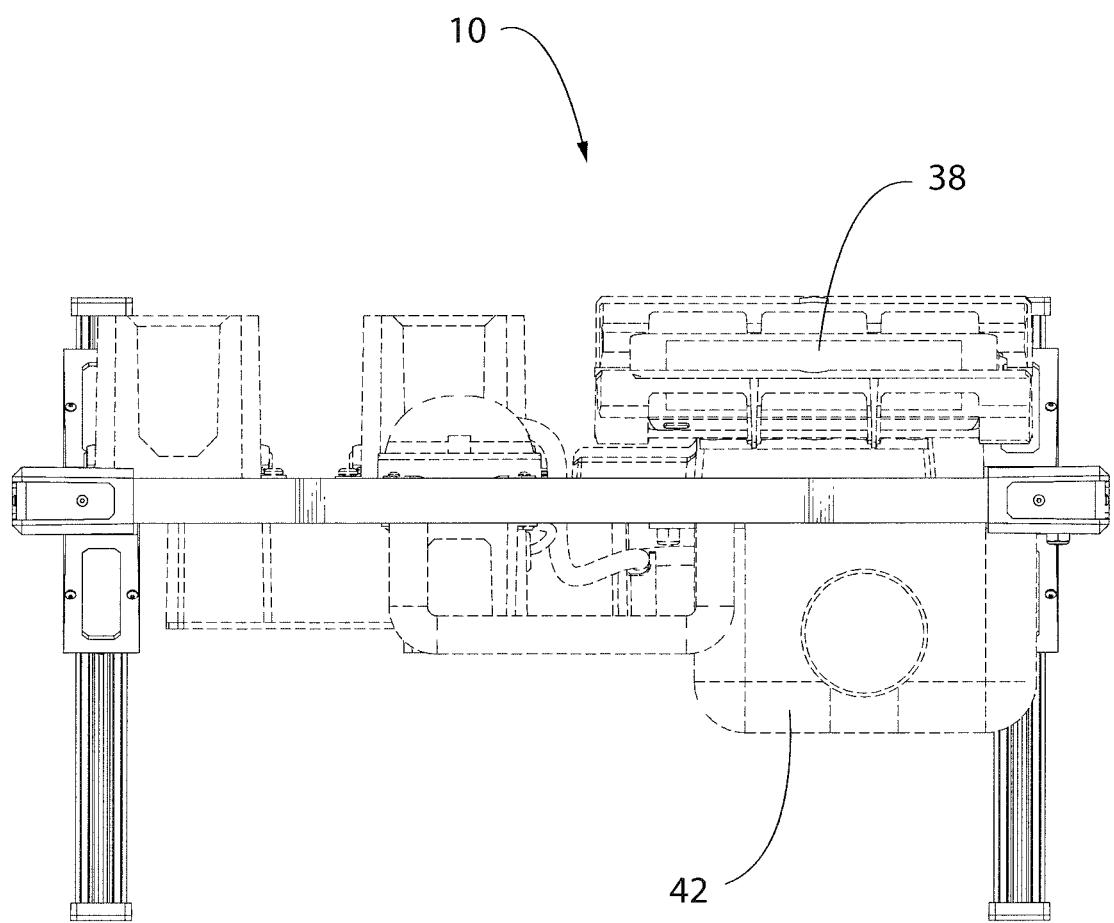
FIG. 10 is a top plan view of the soil-testing apparatus of FIG. 4.
Figure 11:
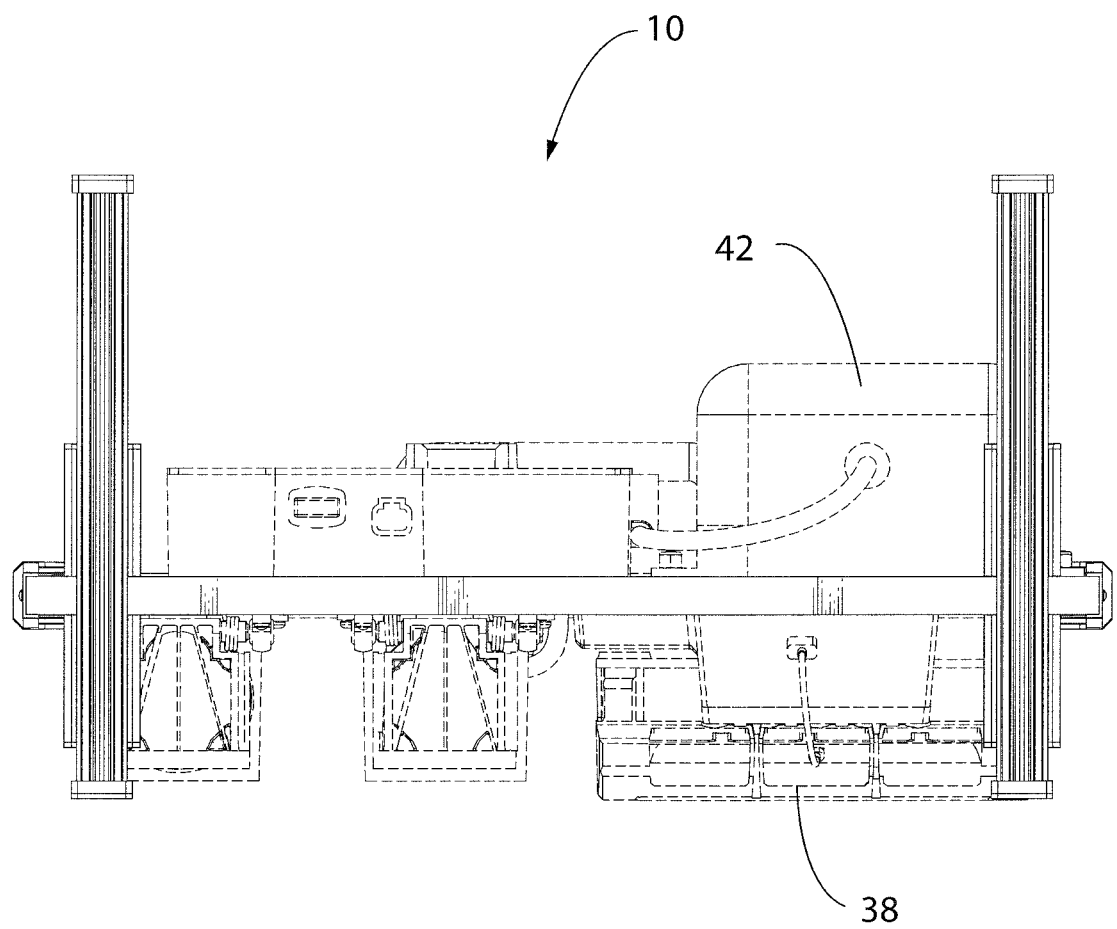
FIG. 11 is a bottom plan view of the soil-testing apparatus of FIG. 4.
Figure 24:
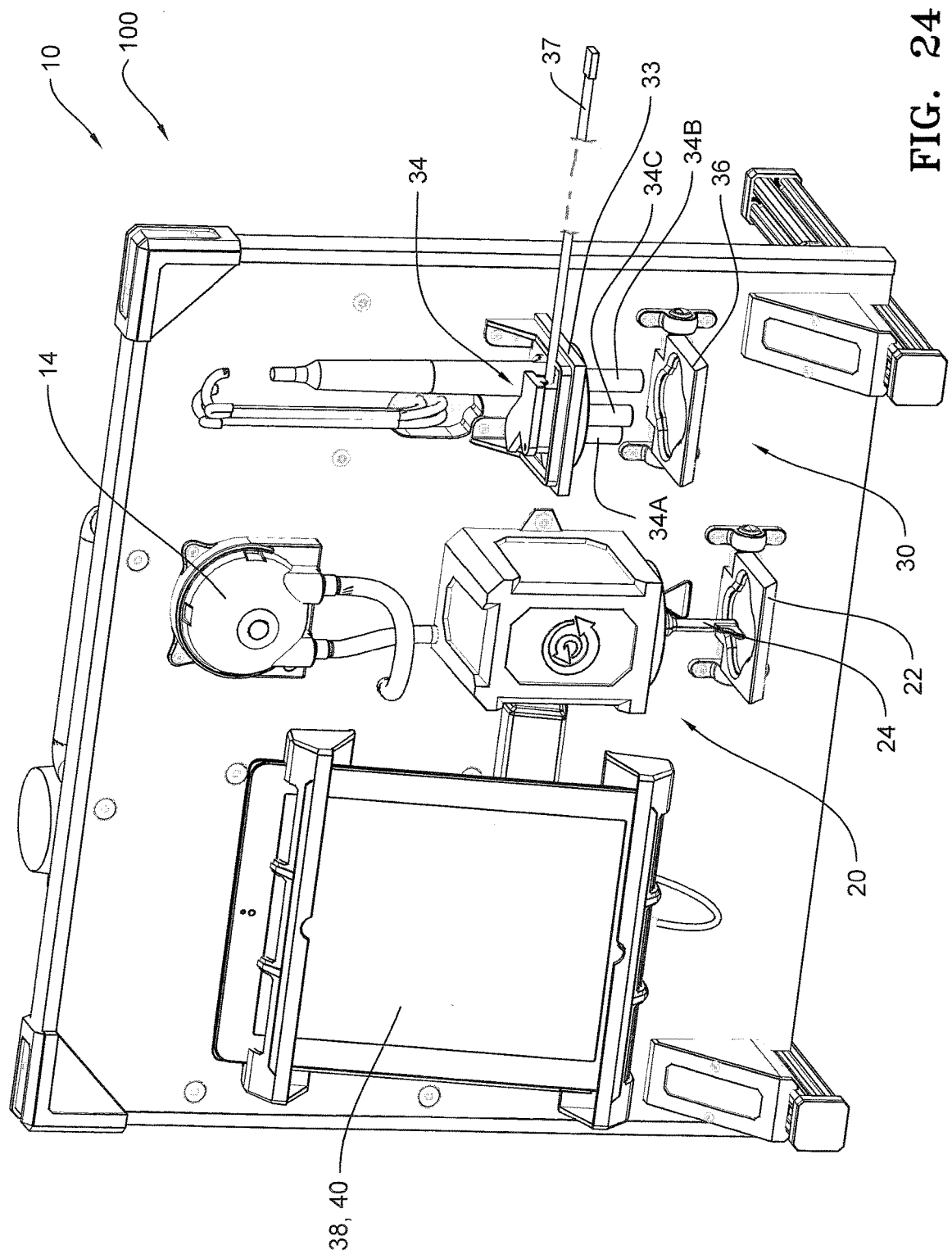
FIG. 24 is front view of another embodiment of a soil testing apparatus.
Figure 25:
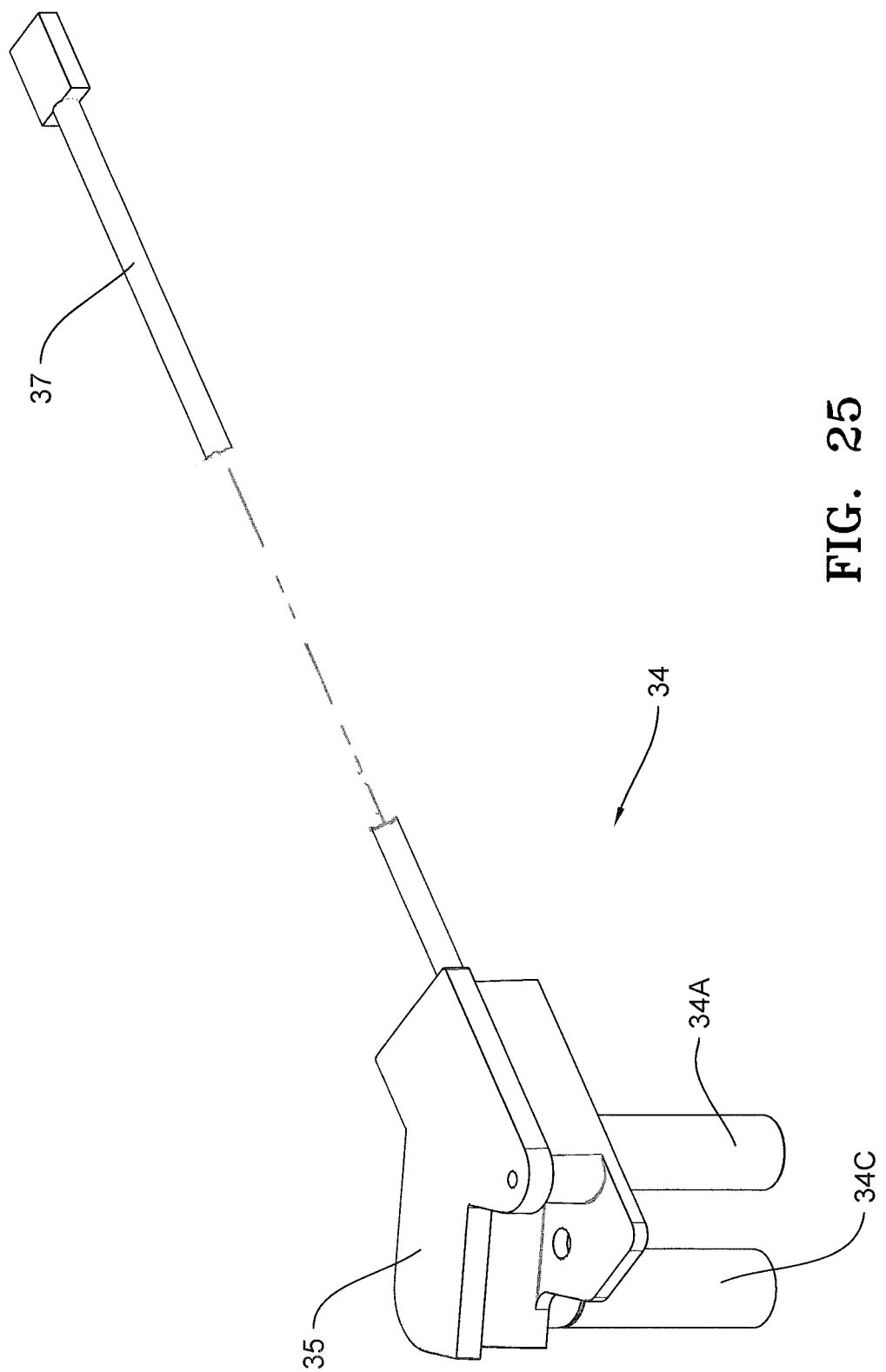
FIG. 25 is a view of the multiple sensor array of the soil testing apparatus of FIG. 24.

Referring to FIGS. 4 and 24, an example of a soil sensing apparatus 10 with a sensor unit 34 comprising an array of multiple sensors is shown for reading multiple soil characteristics. In reference to FIG. 24, the sensor unit 34 has a first ion selective sensor 34A for sensing the nitrate ($NO_3$) ion for a nitrate concentration reading, a second ion selective sensor 34B for sensing the hydrogen ion for a pH reading, and a reference sensor 34C to compare and confirm the results of one or both of the first and second ion selective sensors 34A, 34B. The sensors 34A, 34B and 34C of the sensor unit 34 may be supported by a module 35 in spaced relation, as shown in FIGS. 24 and 25. While a spaced relationship has been shown to provide more stable and accurate readings due to the increased surface area for ion transfer, it is contemplated that various sensors comprising the sensor unit 34 may be in close proximity to each other on one or more modules as demonstrated by the sensor 34 of FIGS. 1-3, which has an integrated ion selective electrode and reference electrode within a single sensor module.

FIG. 25 is an enlarged view of the sensor unit 34 of FIG. 24 wherein the first sensor 34A and reference sensor 34C are supported by module 35. Module 35 may be removably or fixedly secured within soil sensor station 30 by a sensor support member 33. One benefit of removable modules is that repair or replacement of faulty or malfunctioning sensors can be done easily and without significant disassembly or manipulation. Module 35 connects via a cord 37 to a processor on board the soil testing apparatus 10 which then connects to the computing device 38, or the module 35 may connect directly to the computing device 38.

Figure 26:
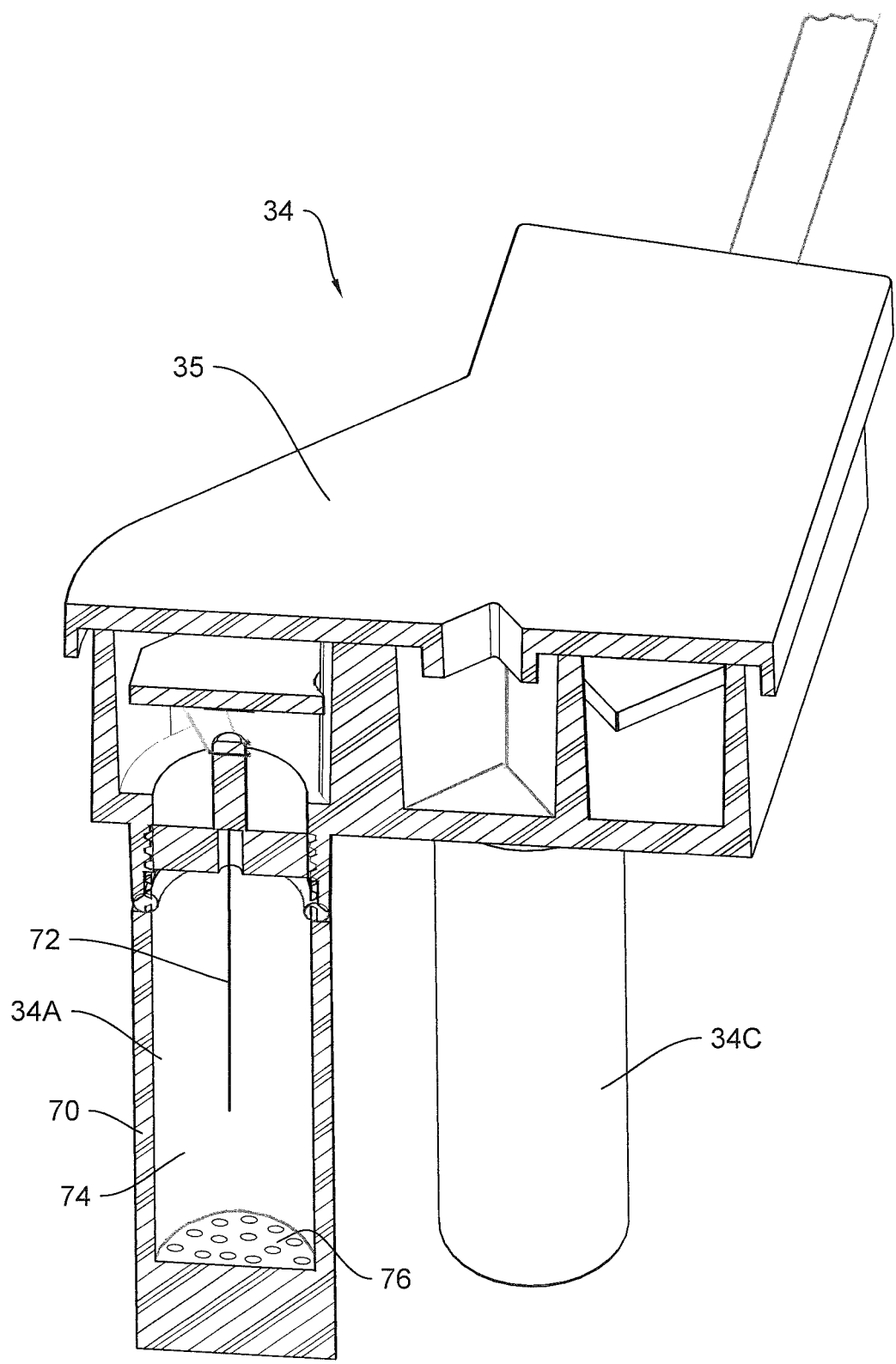
FIG. 26 is a cross-sectional view of a first sensor of the multiple sensor array of FIG. 25.

FIG. 26 shows as a sectional view of the first sensor 34A threadably connected to module 35. First sensor 34A may comprise a housing 70 having a top, a bottom and at least one sidewall. At the top end of the housing 70 is threaded to threadably connect to module 35 which is supported by the sensor support 33 as shown in FIG. 24. Alternatively, the first sensor 34A may independently supported within an aperture of the sensor support 33. As shown in FIG. 26, an electrical lead 72 extends through the top end of housing 70 into an internal cavity 74 containing a conductive solution, which may be, for example, a gel or liquid. Cavity 74 is tightly sealed on both ends to prevent the conductive solution from leaking out. Lead 72 converts the activity of ions, such as the nitrate ion, in the cavity 74 into electric potential for measurement by a voltmeter or pH meter. Nitrate ions enter the cavity 74 from the soil slurry 18 being sampled through a permeable polymer portion 76 affixed to a porous floor on the bottom of housing 70. The electric potential measurement is then converted using a nitrate concentration algorithm into a nitrate reading and displayed on display screen 40.

Referring to FIG. 27, the second sensor 34B comprises a housing 80 having a top, a bottom and at least one sidewall. As shown in FIG. 24, the sensor 34B may be supported within an aperture of the sensor support 33 or it may be threadably connected or otherwise supported by the module 35 similar to the first sensors 34A. As best shown in FIG. 27B, the housing 80 defines an outer cavity 84. Within the outer cavity 84 is a second internal cavity 86. The outer cavity 84 contains a conductive solution, which may be, for example, a gel or liquid. The outer cavity 84 is tightly sealed on both ends to prevent the conductive solution from leaking out. A ceramic permeable disc 87 is disposed in the wall of the housing 80 which allows ions within the soil slurry being sampled to enter into the outer cavity 84. An electrical lead 82 for a reference electrode extends into the electrically conductive solution within the outer cavity 84 and converts the activity of ions, such as the hydrogen ion, in the outer cavity 84 into electric potential for measurement by a voltmeter. The internal cavity 86 has a permeable glass or polymer end 89 which allows hydrogen ions from the soil slurry being sampled to pass into the internal cavity 86. Disposed within the internal cavity 86 is an electrical lead 88 for an ion selective electrode. The electric potential measurement is converted using a pH algorithm into a pH reading and displayed on display 40.

Figure 28:
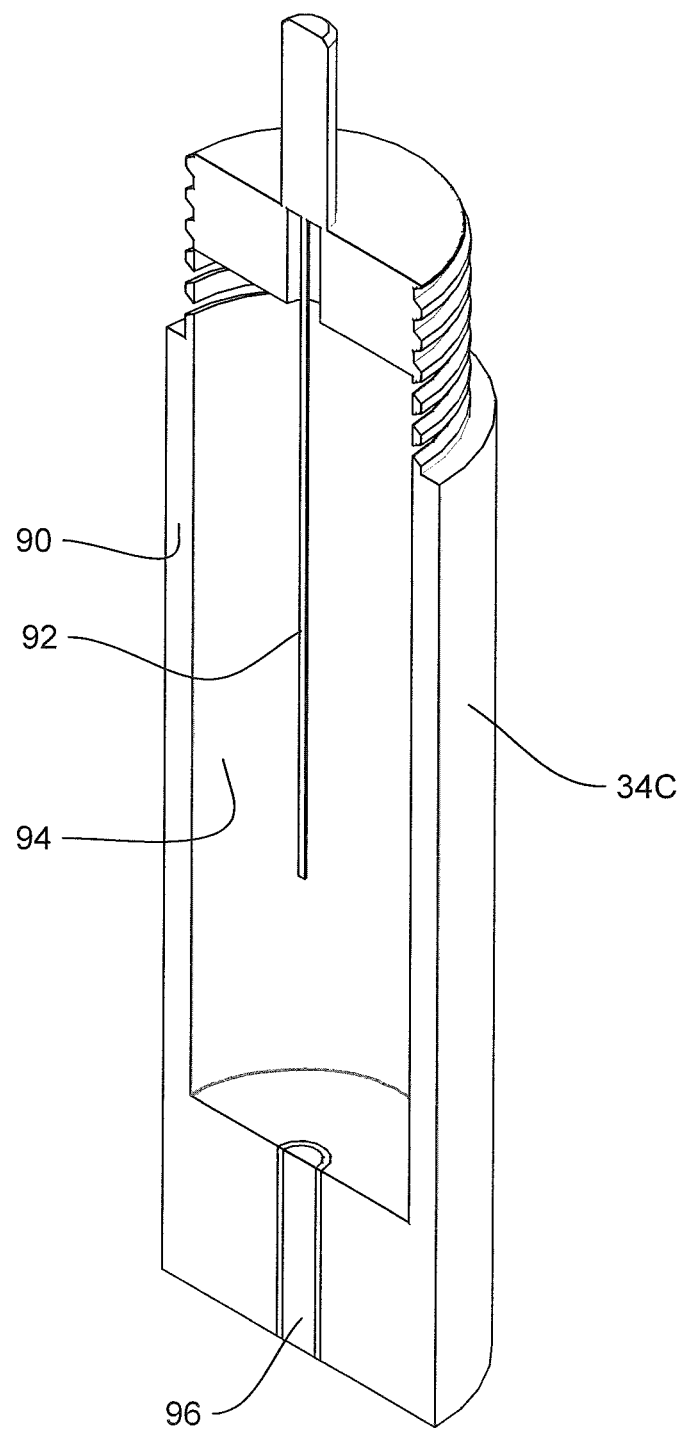
FIG. 28 is a cross-sectional view of the reference electrode of the multiple sensor array of FIG. 25.

Referring to FIG. 28, an embodiment of reference sensor 34C is illustrated. The reference sensor 34C comprises a housing 90 having a top, a bottom and at least one sidewall. The top end is threaded for threadably connecting to module 35. Alternatively, the reference sensor 34C may be supported within an aperture of the sensor support 33. An electrical lead 92 extends into an internal cavity 94 containing a conductive solution, which may be, for example, a gel or liquid. The cavity 94 is tightly sealed on both ends to prevent the conductive solution from leaking out. Lead 92 extends into the cavity 94 and converts the activity of ions in the cavity 94 into electric potential for measurement by a voltmeter or pH meter. Ions enter the cavity from the soil slurry being sampled through a permeable ceramic portion 96 positioned within an opening in the bottom wall of the housing 90. The electric potential measurement is used by the nitrate and/or pH algorithms to refine their respective nitrate and pH values, the refined values are then displayed on the display 40. It should be appreciated that reference sensor 34C may be used in conjunction with any other sensor or sensors in the sensor unit 34 or none at all. For instance, an ion selective electrode may have its own dedicated and/or integrated reference electrode or it may utilize a common reference electrode with other ion selective electrodes of the sensor unit 34.

Figure 29:
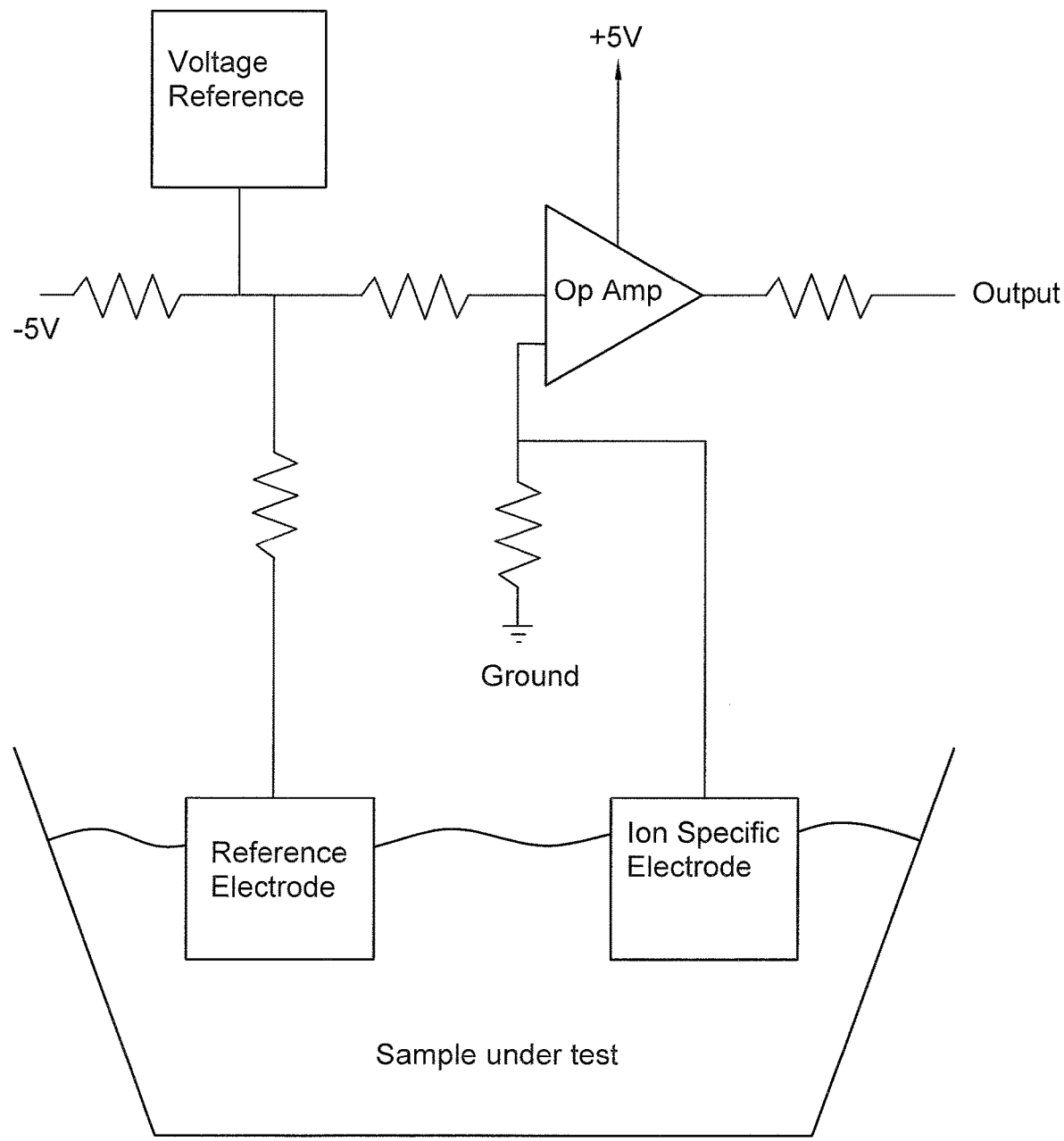
FIG. 29 is a circuit diagram of the soil testing apparatus of FIG. 24.

Referring now to FIG. 29, a circuit diagram of the sensor unit 34 is shown. A voltage amplifier, such as an operational amplifier 100, may be used to amplify the data coming from one or more of the sensors in the sensor unit 34. In FIG. 29, the sensor unit 34 may be coupled to the computing device 38 for processing and data logging by a wired connection; however, the transmission of the amplified data to the computing device 38 may be via a wireless connection.

The apparatus 10 may be optionally mounted to a tractor or other vehicle. Alternatively, the apparatus 10 may be mounted to an autonomous vehicle that includes a soil sampling apparatus. For example, a mobile autonomous device can be programmed to go to a designated spot or series of spots, take soil samples from the field, and automatically analyze the soil for different nutrients, including, but not limited to, potassium, phosphorus, nitrate nitrogen, ammonium nitrogen, manganese, bromide, fluoride, Zinc, boron, molybdenum, salinity, pH, Humus (organic matter), calcium, magnesium, ammonia nitrogen, manganese, aluminum, nitrite nitrogen, sulfur, chloride, ferric iron, and copper by using the appropriate sensor 34, such as, for example: (i) by measuring reflected or transmitted light in the near infrared, mid infrared, or visible light bands for the light corresponding to the desired nutrient; (ii) by using an insertable ion selective electrode for measuring the total ionic activity and ionic activity for the nutrient being measured in the slurry 18; or (iii) by utilizing the laser-induced breakdown spectroscopy method discussed above. Knowing the amount of water being added by the pump 14 also allows for soil salinity levels to be measured using sensors 34, such as a conductivity sensor.

A separate analysis can be performed on each soil sample taken from a particular location. Alternatively, samples taken from multiple locations can be mixed together for analysis. Additionally, the present invention allows for soil to be sampled directly next to plants so that users can obtain data on soil conditions the plants are currently experiencing. The geographic location and depth of soil sample is recorded along with the soil analysis results by the computing device 38. While the soil sample slurry 18 is preferably returned to the ground, it may be desirable to keep the soil sample slurry 18 for later analysis or confirmation of results. In this case, the soil sample slurry 18 may be stored in containers, such as a plastic cup and lid, a plastic bag or any suitable container that can be labeled with a sample identifier. The sample identifier may be a printed on bar code or an applied label containing information related to soil content and sampling location.

Figure 14:
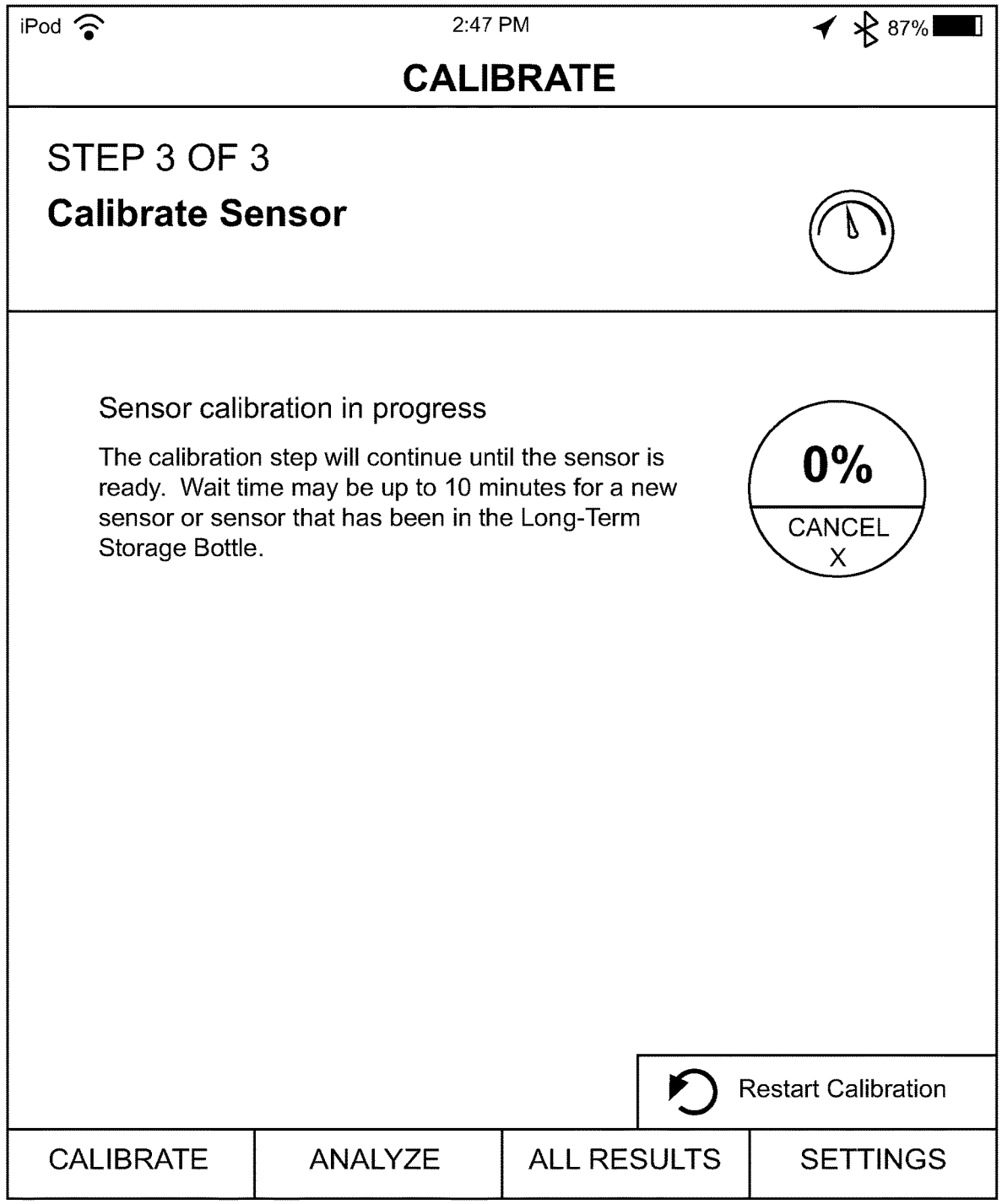
Figure 15:

FIGS. 12-23 illustrate examples of various screens of a user interface for the system 100. Specifically, FIGS. 12-14 illustrate examples for instructing the user to perform a calibration process for the soil testing apparatus. FIGS. 15-18 illustrate examples for instructing the user to prepare a soil sample, identifying the soil sample, and to perform a soil analysis.

Figure 16:
Figure 17:

FIG. 16 illustrates a screen with multiple input fields for identify a particular soil sample. The input fields may include a drop down list of predefined user-selectable options, for example, a predefined listing of selectable names from a "farmer" field 102 to identify the user performing the soil test. The input fields may also include a user-selectable listing of "farm" names 104 to identify the farm from which the soil samples are taken. The input fields may also include a user-selectable listing of "field" names 106 to identify the particular field from which the soil samples are taken. The input fields may also include a user-selectable listing of field analysis 108 allowing a user to label the type of analysis being performed, e.g., nitrogen test, pH test, phosphorous test, etc. The input fields may also include a field in which a soil sample number 110 may be input, and input fields for identify the depth of the soil sample 112, the core length of the soil sample 114, and the latitude 116, longitude 118 and altitude 120 at which the soil sample was taken. The input fields may also permit the user to select a cartographed location of the soil sample 122 which will then populate the latitude, longitude and altitude fields. The input fields may also include a notes field 124 for adding relevant information pertaining to a soil sample.

Figure 18:

FIG. 18, is an example of an output screen 200 identifying the results of the analysis of the soil sample. In this example, the analysis determined that the nitrate level of the soil sample was 20 parts per million (ppm) which may be displayed numerically as in output field 202 and/or graphically as in output field 204.

FIG. 19 is an example of an "All Results" screen, which, as the name implies, displays all of the soil test results stored in memory. The soil test results may be exported to other applications such as an Excel spreadsheet, for example.

Soil-Sampling Locations

The selection of locations for conducting soil sampling can be performed in one of the following manners: (i) a farmer randomly selects sampling locations; (ii) a crop advisor generates a sampling map while in the field; or (iii) a crop model identifies sampling locations.

The system 100 may identify the fewest number of locations for soil sampling as is necessary to minimize farmer time and effort while still ensuring that sufficient soil samples are obtained for analysis. In another embodiment, a crop model may identify the optimal number of soil samples for obtaining a sufficient soil samples for analysis.

Alternatively, the system 100 may receive instructions from a user that identifies soil sample locations. Alternatively, the system 100 may independently generate sampling locations while in the field based on various agronomic factors such as soil data, soil type, Carbon:Nitrogen (C:N) ratios, Carbon, tillage practices, weather, seed data including seed type, as-applied planting data such as plant population and row spacing, as-applied fertilizer data, topography (slope), and zone characteristics to generate soil-sampling locations. The system may also analyze spatial and temporal relationships and patterns using the aforementioned agronomic factors within a field, between zones or within a zone to determine soil sampling locations. The soil sampling locations may be determined within a zone or zones based upon the slope and the size of the zone. Alternatively, the soil sampling locations within a zone may be determined based on projected high and low Nitrogen balances. Any number of other agronomic factors may be used in this manner to determined soil sampling locations.

The system may also analyze the aforementioned agronomic factors to further generate and display to a user spatial and temporal relationships and patterns within a field, between zones or within a zone. Examples of these relationships and patterns include slope, size of a zone, plant population, Normalized Difference Vegetation Index (NDVI), plant extractable soil water, projected high and low Nitrogen balances. Any number of other agronomic factors may be analyzed to generate and display spatial and temporal relationships and patterns. The user can then select soil sampling locations based on these relationships and patterns, or as mentioned in previously, allow the system to analyze the relationships and patterns and determine soil sampling locations.

Once the locations are determined, the system 100 may display the locations and provide directions to the locations using GPS. The directions can be shortest route, fastest route, least amount of obstacles (waterways, creeks, hills). The directions may be visual or audio. The GPS may be a distinct component integrated into the apparatus or may utilize the GPS capabilities of a tablet or smartphone.

Generating Crop Nutrient Prescriptions

Once the nutrient content of a soil sample is determined and associated with the results of a sufficient number of other soil samples for a field or particular zone within a field, the system 100 may be used to generate a crop nutrient prescription for the field or zone using numerous algorithms (discussed later) which take into account several agronomic factors or variables which the user may input through the user interface, including, for example, the crop species being grown (i.e., corn, soybeans, etc.), the desired yield or yield potential, the growth stage of the crop, the results of the soil analysis, and the percentage of organic matter within the soil. The algorithms may take into account various other agronomic factors, such as, soil type, Carbon:Nitrogen (C:N) ratios, Carbon, tillage practices, weather, seed data including seed type, as-applied planting data such as plant population and row spacing, as-applied fertilizer data, topography (slope), hours of daylight, and zone characteristics, the nature of past and future chemical treatments, the form and quantity of anticipated current chemical treatment.

Figure 20:
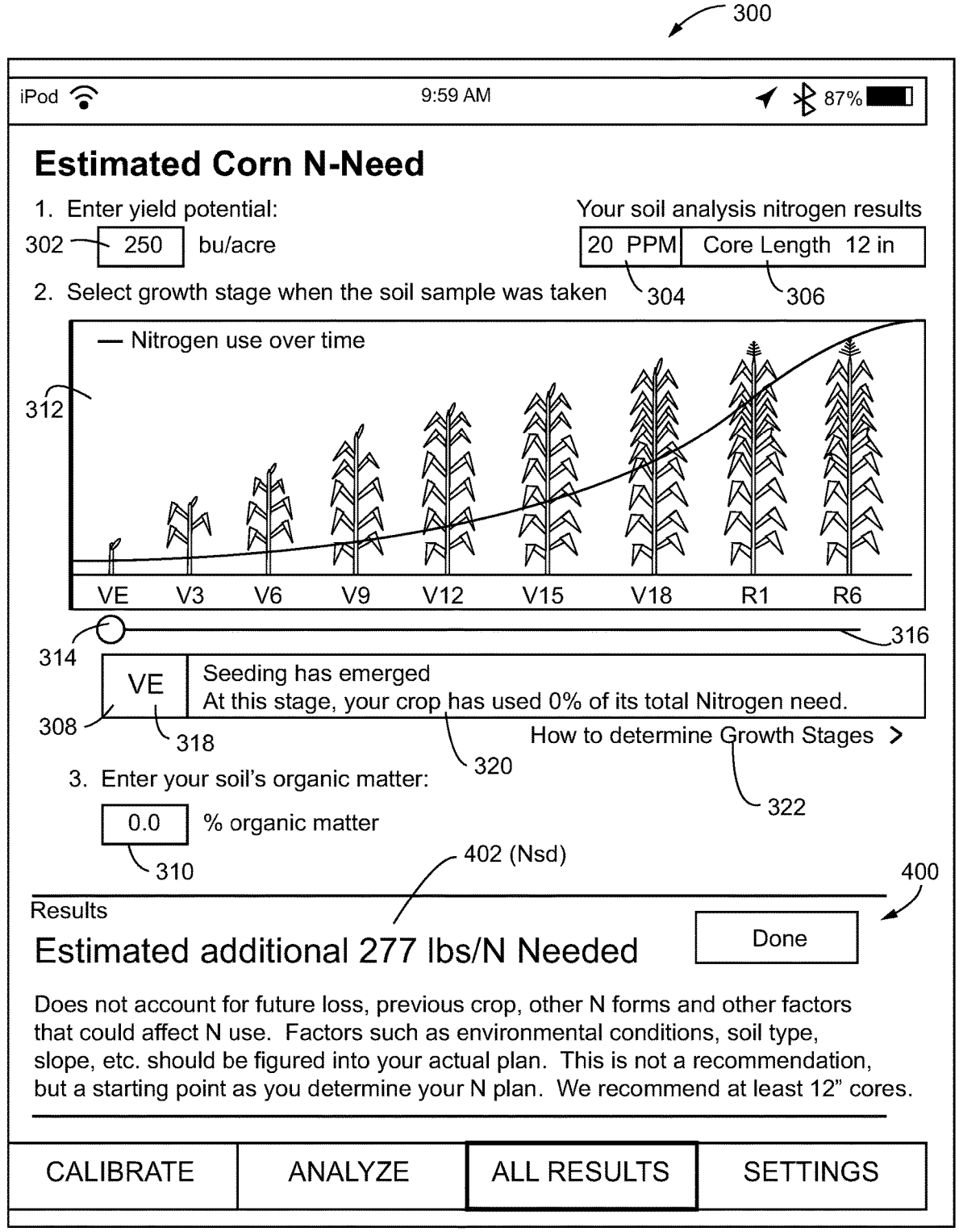

One example of a user input screen is illustrated in FIG. 20 identifying various user input fields, include yield potential 302, the soil analysis results 304, the core length of the soil samples 306, the growth stage when the soil sample was taken 308, and the percentage of organic matter 310. The other agronomic factors referenced above which may also be taken into account in generating the crop nutrient prescription (e.g., weather conditions, hours of daylight, the nature of past and future chemical treatments, and the form and quantity of anticipated current chemical treatment) are not shown in FIG. 20 but may be manually input through similar user input fields or automatically input by integrating with other database systems. For example the system may interface with a weather database to take into account weather conditions for the particular field or zone based on the GPS coordinates or field identifiers previously entered as discussed above. Similarly, the hours of daylight may be generated based on an internal clock and the GPS location. Additionally, the nature of past and future chemical treatments and the form and quality of chemical treatments may be manually inputted or may be derived from a database containing crop nutrient management information from prior years.

Continuing to refer to FIG. 20, the input screen may display information to assist the user in entering correct data into the appropriate fields. For example, the growth stage input field 308 for when the soil sample was taken may include a window 312 showing crops at various stages of growth so the user can compare the crops in the field with the images to select the appropriate growth stage. For example, the growth stage of corn may include representations of the corn plant at the VE stage through the R6 stage. The user may be able to drag an indicator 314 along a track 316 to position the indicator under the corresponding growth stage, and another window 318 may be provided which displays the selected growth stage and another window 320 which provides a description or explanation of the growth stage selected to ensure that the user has selected the appropriate growth stage. Input screens 300 may include hyperlinks 322 to assist the user in determining growth stages, for example by a user selecting the hyperlink 322 a new window may be opened on the screen to provide illustrations and/or a tutorial to assist the user in determining the growth stage.

As illustrated in FIG. 21, if a necessary input field is not filled in, the program may prompt a user to input information into the field before allowing the user to input other fields or before generating the crop nutrient prescription.

Referring again to FIG. 20, a results screen 400 may be displayed below the input screen 300 that identifies the crop nutrient prescription 402 needed to achieve the desired yield potential 302 previously entered based on the other input variables 304, 306, 308, 310. In the example of FIG. 20, the results screen 400 displays that an additional 277 lbs of Nitrogen are needed to achieve the desired yield input 302 (of 250 bushels per acre) based on the soil analysis results 304 (of 20 ppm of nitrogen in the soil), at a growth stage 308 (of VE) and an organic matter percentage 310 (of 0.0%).

Figure 22:
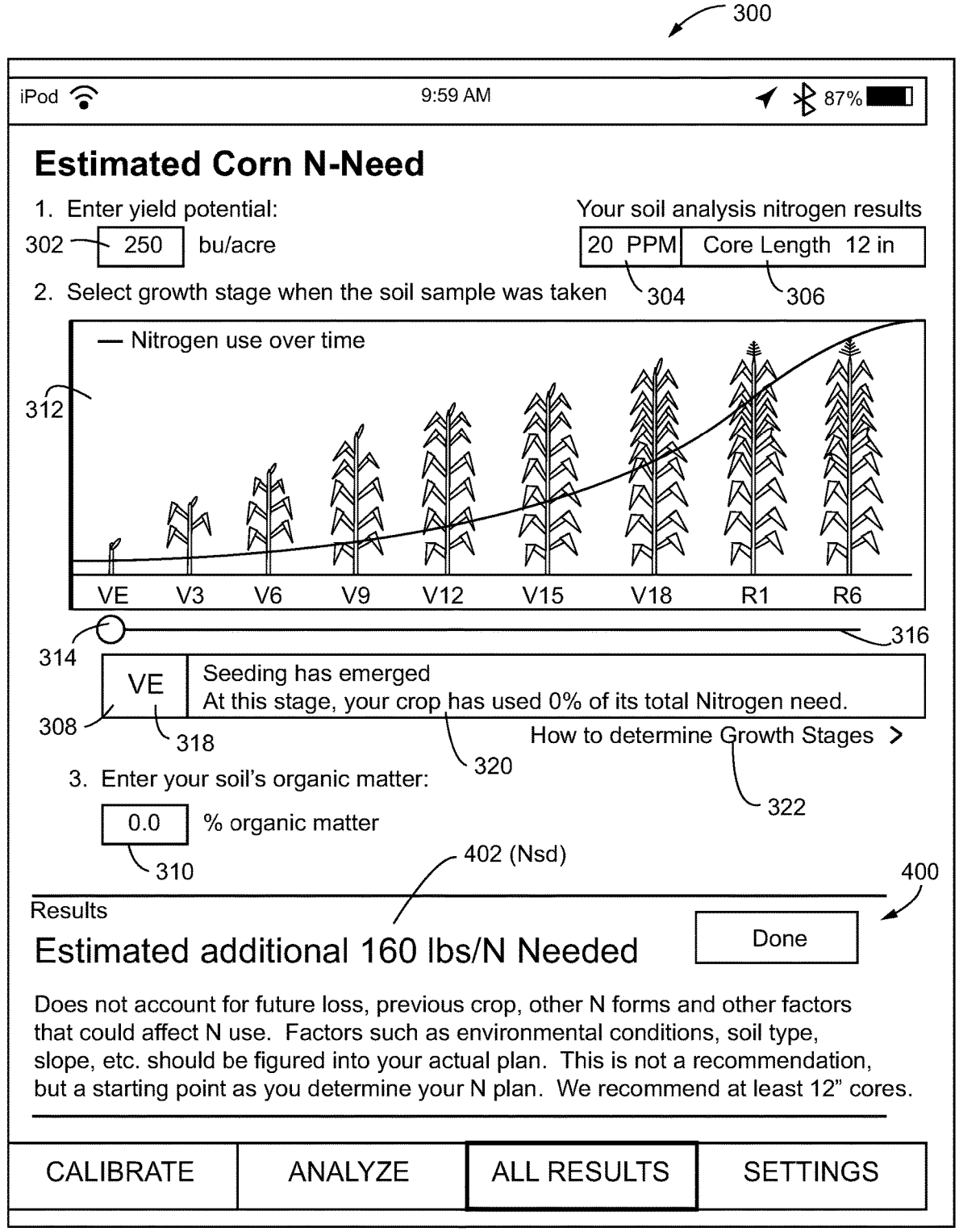

FIG. 22 is similar to FIG. 20, with the same input variables of desired yield 302 (of 250 bu/acre), soil nitrogen results 304 (of 20 ppm), core length 306 (of 12 inches), and growth stage 308 (of VE) except that the input variable for the organic matter 310 was changed from 0% to 3%, resulting in the nutrient prescription 402 of the results screen 400 changing from 277 lbs Nitrogen needed to 160 lbs Nitrogen needed.

Figure 23:
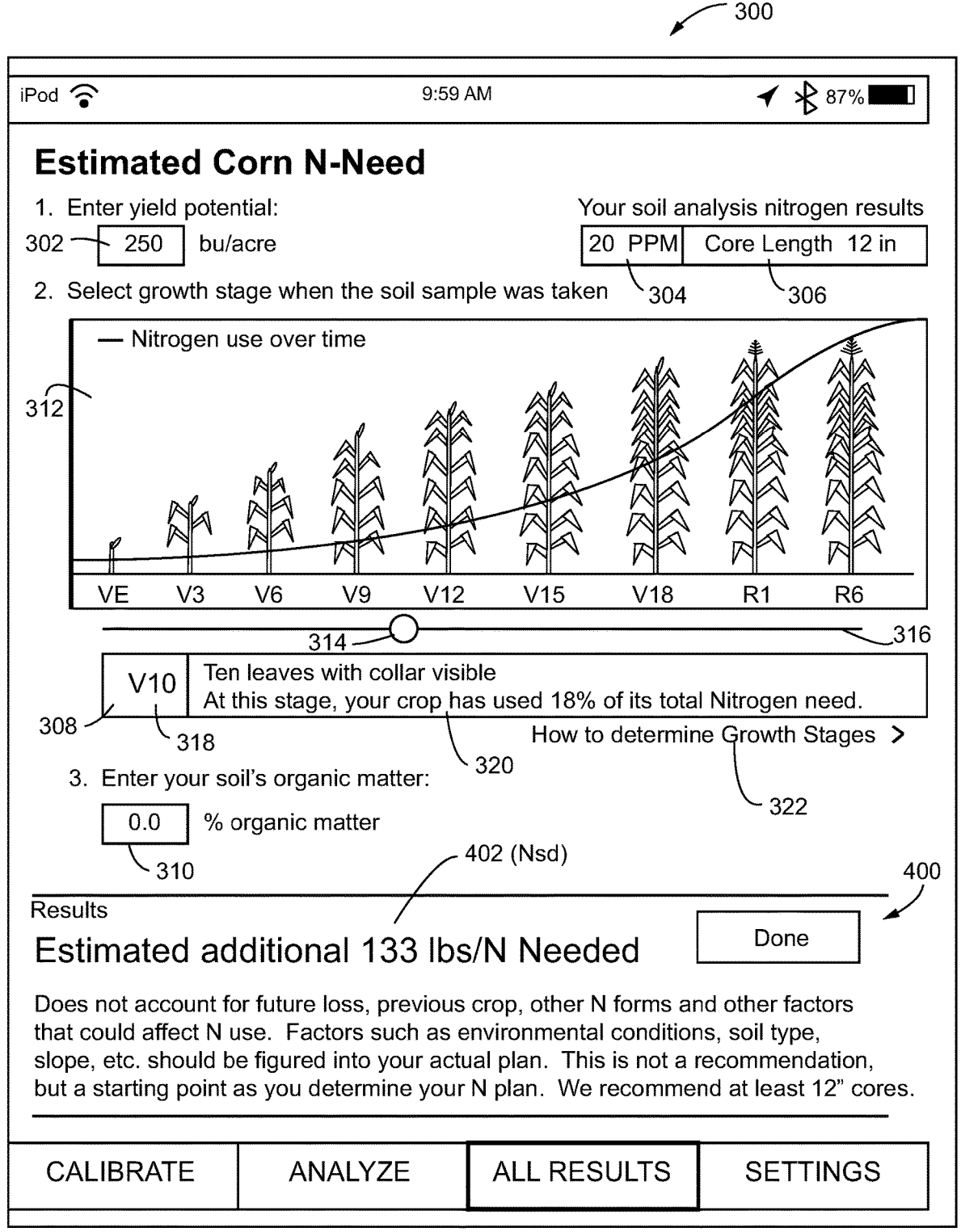

FIG. 23 is similar to FIG. 22, with the same input variables of desired yield 302 (of 250 bu/acre), soil nitrogen results 304 (of 20 ppm), core length 306 (of 12 inches), and organic matter 310 (of 3%), except that the growth stage 308 was changed from VE to V10, resulting in the nutrient prescription 402 of the results screen 400 changing from 160 lbs Nitrogen needed to 133 lbs Nitrogen needed.

Process for Generating Crop Nutrient Prescriptions

To generate the crop nitrogen prescriptions 402 shown in the results screen 400, the system 100 is configured to analyze the soil sample and various agronomic factors to generate a crop nutrient prescriptions.

The total nitrogen application plan for a crop ($N_{ap}$) is determined as follows:

$$N_{ap} = Y * K_{gf}$$

Where:
$K_{gf}$ is a constant used to estimate the total application plan of nitrogen for a crop;
Y is the yield target for the crop.

The value of the grower factor constant ($K_{gf}$) can be varied in order to achieve different application plans and is known in the art as being between 0 to 1.5 lbs. of nitrogen per bushel of expected yield. One skilled in the art will recognize that different $K_{gf}$ values will be necessary for different crop species, crop rotation, crop varieties, number of growing degree days (GDDs), and climate, among other factors. The value of the grower factor constant ($K_{gf}$) may be established as 1.11 for corn. If the yield target (Y) is 200 bu/acres (bushels per acre) of corn, the corresponding total application plan of a nutrient for a crop ($N_{ap}$) would be 222 lbs/acre.

The available nitrogen in soil ($N_{sa}$) may be determined by converting the results of the soil test from ppm to lbs/acre using conversion factor ($K_{cf}$) derived from the depth ($D_{in}$) of the soil sample (also referred to as the core length). The current availability of a nitrogen in the soil ($N_{sa}$) may be determined as follows:

$$N_{sa} = N_{nr} * K_{cf}$$

Where:
$N_{nr}$ is the nitrogen reading of the soil;
$K_{cf}$ is the conversion factor based on sampling depth and units of measurements.

The conversion factor ($K_{cf}$) is determined as follows:

$$K_{cf} = (D_{in}/6.67) * 2$$

Where:
$D_{in}$ is the sampling depth, in inches.

For example, a nitrogen reading of 20 ppm from a soil sample taken at a depth of 12 inches, would convert to approximately 71.964 lbs/acre.

The amount of a nitrogen that a crop requires to reach yield-target maturity over an entire growing season ($N_{yt}$) is determined as follows:

$$N_{yt} = Y * (N_{ap}/Y)$$

Where:
Y is the yield target for the crop;
$N_{ap}$ is the total application plan of nitrogen for a crop (as calculated above).

The amount of a nitrogen the crop requires to reach yield-target maturity from its current growth stage ($N_{gs}$) may be determined as follows:

$$N_{gs} = N_{yt} - ((K_\%/100) * N_{yt})$$

Where:
$N_{yt}$ is amount of a nitrogen that a crop requires to reach yield-target maturity over an entire growing season (as calculated above);
K % refers to the estimated percentage of nitrogen consumed at a given growth stage based on the total nitrogen requirements of the crop over a complete growing season.

The corresponding values in Table 1 of FIG. 30 may be used to estimate the $K_\%$ values for the consumption of nitrogen by corn over a complete growing season and may be derived from Bender R R, Haegelle J W, Ruffo M L, Below F E, (2013) *Modern Corn Hybrids' Uptake Patterns. Better Crops* 97:7-10, incorporated herein in its entirety by reference. For example, referring to Table 1, at the V6 growth stage, corn will have consumed an estimated 8% of its total nitrogen requirements for a complete growing season.

The soil deficiency with respect to the amount of nitrogen the crop requires to reach yield-target maturity from its current growth stage ($N_{sd}$) may be determined as follows:

$$N_{sd} = N_{gs} - N_{sa}$$

Where:
$N_{gs}$ is the amount of nitrogen the crop requires to reach yield-target maturity at its current growth stage (as calculated above);
$N_{sa}$ is the current availability of nitrogen in the soil (as calculated above).

For example, if the amount of nitrogen a crop requires to reach yield-target maturity at its current growth stage ($N_{gs}$) is 204.24 lbs/acre and the current availability of nitrogen in the soil ($N_{sa}$) is 71.964 lbs/acre, the soil deficiency with respect to the amount of nitrogen the crop requires to reach yield-target maturity from its current growth stage ($N_{sd}$) would be 132.276 lbs/acre.

This information does not, however, take into consideration potential nitrogen from nitrification or mineralization. They also do not take into consideration potential nitrogen loss from leaching or denitrification or volatization. A user can utilize this information a general guideline with the understanding that there are factors that are not taken into consideration that could affect the total amount of nitrogen needed from the time of soil sampling until physiological maturity.

To account for mineralization, the nitrogen prescription for the crop to reach yield-target maturity ($N_{ca}$) may be determined as follows:

$$N_{ca} = N_{sd} - N_{fm}$$

Where:

$N_{sd}$ is the soil deficiency with respect to the amount of nitrogen the crop requires to reach yield-target maturity from its current growth stage;

$N_{fm}$ is the estimated future mineralization of nitrogen.

Future mineralization ($N_{fm}$) refers to amounts of nitrogen that are expected to become available in the soil for crop growth due to natural processes, such as, for example, the breakdown of organic matter. The future mineralization ($N_{fm}$) is determined as follows:

$$N_{fm} = N_{mp} - N_{pm}$$

Where:

$N_{mp}$ is the mineralization potential for nitrogen;

$N_{pm}$ is the estimated amount of nitrogen previously mineralized.

The nitrogen mineralization ($N_{fm}$) could be further modified and refined when calculating nitrogen requirements based on the C:N ratio (i.e., the ratio of carbon to nitrogen).

The mineralization potential for nitrogen ($N_{mp}$) is determined as follows:

$$N_{mp} = (K_{om} * K_{\%\,n}) * 100$$

Where:

$K_{om}$ is the estimated percent of organic matter in the soil sample;

$K_{\%\,n}$ is the estimated amount of nitrogen present per percent of organic matter present in the soil sample.

The estimated percent of organic matter in the soil sample ($K_{om}$) may be provided by the user and may be in the range of 0-5% and the estimated amount of nitrogen present per percent of organic matter present in the soil sample ($K_{\%\,n}$) may be a pre-programmed constant in the range of 10-30 lbs/acre per percent organic matter. For example, if the estimated percent of organic matter in the soil sample ($K_{om}$) is 2% (or 0.02) and the estimated amount of the nutrient present per percent of organic matter present in the soil sample ($K_{\%\,n}$) is 15 lbs/acre, the nitrogen mineralization potential ($N_{mp}$) would be 30 lbs/acre.

Prescription Model Variables:

As mentioned previously, the nitrogen mineralization $N_{fm}$ could be further modified and refined when calculating nitrogen requirements based on the C:N ratio (i.e., the ratio of carbon to nitrogen). The system may collect various user inputs of agronomic factors such as soil type, topography (specifically, slope), weather, seed variety, temperature, tillage data, tillage practices, tons of biomass from previous crop, previous crop harvest dates and original C:N ratios. Using these inputs, the system can determine existing, current and projected values for the following factors: temperature, growing degree days, growth stage, inches of precipitation, soil moisture, plant $H_2O$ uptake, currently available biomass, amount of $CO_2$ released, percentage carbon in original and current biomass, pounds of carbon from original and current biomass, pounds of nitrogen from original and current biomass, soil nitrogen balance, current C:N ratios and soil state.

The system may utilize a C:N model, such as is disclosed in U.S. Provisional Patent Application No. 62/152,623 for Agronomic Systems, Methods and Apparatuses, which is hereby incorporated by reference in its entirety.

The system may model the weather, including temperature and inches of precipitation on a yearly, monthly, weekly, daily or hourly basis. Weather may have a significant impact on the uptake of nutrients such as nitrogen by crops. In particular, temperature and moisture can impact the amount of nitrogen mineralized from the organic matter fraction of the soil. Excessive rainfall may cause nitrogen loss through leaching and saturation of the soil, causing the plant to run out of nitrogen prior to reaching rapid vegetative growth stages such as the V8 stage. Colder temperatures, such as those below 50 degrees Fahrenheit, generally cause soil microbial activity to be significantly slowed or stopped altogether. Excessively dry conditions may prevent nitrogen from moving from the point of application to the root zone of the plants.

The system may also utilize historical weather, such as is disclosed in U.S. Provisions Patent Application No. 62/054,870 for Agronomic Systems, Methods and Apparatuses, which is hereby incorporated by reference in its entirety.

Analysis and Recommendations:

Nitrogen Deficiencies or Surpluses

Using the above factors, the system 100 may determine an optimum C:N ratio to prevent immobilization, an optimum C:N ratio for mobilization, and the minimum volume of a nutrient (namely, nitrogen) that must be added to prevent immobilization. Thus, a user would be able to easily and rapidly determine whether a nitrogen deficiency or a nitrogen surplus is present. If the farmer is encountering a nitrogen deficit, the system can instruct the farmer how many pounds of nitrogen should be added to prevent immobilization. If the farmer is encountering a nitrogen surplus, the system can instruct the farmer to reduce or eliminate future nitrogen addition, thereby saving the farmer time, money and reducing the likelihood runoff nitrogen due to excess application.

Form of Nitrogen Applied and Nitrogen Stabilizers:

The system may evaluate the use of nitrogen stabilizers and the form of nitrogen applied (e.g., ammonia or nitrate) and make recommendations on the use of nitrogen stabilizers and the form of nitrogen applied. Common nitrogen fertilizers include anhydrous ammonia, urea-ammonium nitrate solutions, granular urea, ammonium nitrate and ammonium sulfate. Ammonium ($NH_{4+}$) forms of nitrogen bind to negatively charged soil particles and are not subject to leaching or denitrification losses. This means that applying nitrogen fertilizers that include more ammonium and less nitrate forms of nitrogen reduces the potential for loss in the short term. However, over time, soil microbes convert the ammonium to nitrate ($NO_{3-}$), which can be lost due to leaching or saturation during heavy or excessive rainfall. Urea-based fertilizers are also subject to loss through volatilization when surface applied. Volatilization potential is reduced when the urea is taken into the soil through rainfall, irrigation or tillage.

The system may analyze both short-term and long-term nitrogen needs of a crop while also considering the impact of current and historical weather and make a recommendation as to the form of nitrogen to be used at the next application. If the system identifies a short-term need for nitrogen, it may recommend a form of nitrogen capable of absorption during the time period in which the shortfall is occurring, such as higher nitrates. If the system identifies a long-term need for nitrogen, however, it may recommend a fertilizer with greater amounts of ammonium to reduce potential for short-term loss.

The system may evaluate and recommend the use of nitrogen stabilizers. Nitrogen stabilizers or additives are often added along with to nitrogen fertilizers to slow the rate of conversion from ammonium to nitrate and reduce the risk of loss due to leaching or dentrification. The system can match a specific nitrogen fertilizer with a corresponding nitrogen stabilizer to ensure effectiveness of the fertilizer with the stabilizer. For example, some oil-soluble stabilizers with nitrapyrin pyridine are known to work better with anhydrous ammonia, dry ammonium and urea fertilizers. Other stabilizers work with urea and urea-ammonium nitrate solutions to prohibit urease and allow more time for the urea to be moved into the soil with rainfall. Still other stabilizers only allow the nitrogen to release when the soil warms. The system can aid in planning the application of such time-release stabilizers to minimize nitrogen losses due to volatility.

The details and features of the disclosed embodiments are not intended to be limiting, as many variations and modifications will be readily apparent to those of skill in the art. Accordingly, the scope of the present disclosure is intended to be interpreted broadly and to include all variations and modifications coming within the scope and spirit of the appended claims.

The invention claimed is:

1. A method for generating crop nutrient prescriptions with a portable soil testing apparatus, the method comprising:
   (a) transporting a portable soil testing apparatus in proximity to a field for which a crop nutrient prescription is desired, the portable soil testing apparatus having:
      (i) a pump for delivering a calibrated amount of water from a water source to a cup;
      (ii) a stirring station having a motorized stirring rod;
      (iii) a soil sensing station having at least one soil sensor to measure a soil property;
   (b) collecting a plurality of soil samples within a field zone of the field and recording a GPS location of where each soil sample was collected in the field zone;
   (c) placing a quantity of soil from one of the plurality of collected soil samples into a cup;
   (d) actuating the pump to deliver a calibrated amount of deionized water to the cup containing the soil quantity;
   (e) placing the cup with the soil quantity and calibrated amount of deionized water in the stirring station;
   (f) inserting the stirring rod into the cup and actuating the motor to stir the soil quantity and calibrated amount of deionized water to create a soil slurry within the cup;
   (g) inserting the at least one soil sensor into the soil slurry within the cup, the at least one soil sensor identifying soil properties of the soil slurry;
   (h) via a computing device in signal communication with the at least one soil sensor, associating and storing in memory the identified soil properties of the soil slurry with the recorded GPS location of where the collected soil sample was collected;
   (i) repeating steps (c)-(h) for each of the plurality of collected soil samples;
   (j) via the computing device, generating a crop nutrient prescription for the field zone based on the identified soil properties of the plurality of collected soil samples.

2. The method of claim 1, further comprising:
   via the computing device, inputting agronomic factors of the field zone in which the plurality of soil samples are collected.

3. The method of claim 2, wherein the step of generating a crop nutrient prescription for the field zone is based on the identified soil properties of the collected soil samples and the inputted agronomic factors.

4. The method of claim 3, wherein the identified soil properties include at least one of the group consist essentially of: mineral content, salinity, pH levels, humus content and moisture content.

5. The method of claim 4, wherein the inputted agronomic factors include a plurality of factors selected from the group consisting essentially of: size of the field zone, soil types within the field zone, topography of the field zone, crop species being grown in the field zone, desired yield or yield potential, growth stage of the crop within the field zone, tillage practices within the field zone, weather, plant population within the field zone, row spacing of the crop within the field zone and fertilizer types and amounts applied within the field zone.

6. The method of claim 5, wherein the generated crop nutrient prescription comprises a total nitrogen application plan for a crop based on the amount of nitrogen the crop requires to reach yield-target maturity at its current growth stage and the identified soil properties of the collected soil samples.

7. The method of claim 1, further comprising:
   generating a sampling map to identify locations within the field zone for collecting the soil samples based on agronomic factors of the field zone.

8. The method of claim 7, wherein the agronomic factors include a plurality of factors selected from the group consisting essentially of: size of the field zone, soil types within the field zone, topography of the field zone, tillage practices within the field zone, weather, plant population within the field zone, row spacing of the crop within the field zone and fertilizer types and amounts applied within the field zone.

9. The method of claim 8 wherein the generated sampling map identifies an optimal number of locations for collecting soil samples within a field zone based on the agronomic factors and spatial considerations.

* * * * *